(12) United States Patent
Nishida et al.

(10) Patent No.: US 11,638,531 B2
(45) Date of Patent: May 2, 2023

(54) BLOOD PRESSURE MEASURING DEVICE AND METHOD OF MANUFACTURING BLOOD PRESSURE MEASURING DEVICE

(71) Applicants: OMRON CORPORATION, Kyoto (JP); OMRON HEALTHCARE CO., LTD., Muko (JP)

(72) Inventors: Tomoyuki Nishida, Kyoto (JP); Hirokazu Tanaka, Otsu (JP); Noboru Kohara, Okayama (JP); Shinji Mizuno, Yasu (JP); Kotaro Kitajo, Saitama (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 7 days.

(21) Appl. No.: 16/930,130

(22) Filed: Jul. 15, 2020

(65) Prior Publication Data

US 2020/0345247 A1 Nov. 5, 2020

Related U.S. Application Data

(63) Continuation of application No. PCT/JP2019/000343, filed on Jan. 9, 2019.

(30) Foreign Application Priority Data

Jan. 15, 2018 (JP) .............................. JP2018-004448

(51) Int. Cl.
*A61B 5/021* (2006.01)
*A61B 5/022* (2006.01)
(Continued)

(52) U.S. Cl.
CPC ........ *A61B 5/02141* (2013.01); *A61B 5/0225* (2013.01); *A61B 5/0235* (2013.01);
(Continued)

(58) Field of Classification Search
CPC ............ A61B 5/02141; A61B 5/02233; A61B 5/0225; A61B 5/0235; A61B 5/681;
(Continued)

(56) References Cited

U.S. PATENT DOCUMENTS

| 2006/0058689 A1* | 3/2006 | Kishimoto | ......... A61B 5/02233 |
| | | | 600/490 |
| 2008/0119744 A1* | 5/2008 | Yang | .................. A61B 5/02233 |
| | | | 600/490 |

(Continued)

FOREIGN PATENT DOCUMENTS

| JP | S63-197509 U | 12/1988 |
| JP | H02-82305 U | 6/1990 |

(Continued)

OTHER PUBLICATIONS

Machine Translation of JP2014033829A (Year: 2014).*

(Continued)

*Primary Examiner* — Alex M Valvis
*Assistant Examiner* — Chanel J Jhin
(74) *Attorney, Agent, or Firm* — Oliff PLC

(57) ABSTRACT

The blood pressure measuring device includes a device main body configured to form a flow path of a fluid and supply the fluid, and a cuff to be wound around a living body, the cuff provided with a bag-shaped connection portion with an opening and a connection plate with a hole communicating with the opening; the connection portion formed of a sheet member; the connection plate having a bending elastic modulus higher than that of the connection portion, bonded to the connection portion and adhered to the device main body; and the cuff configured to be inflated when the fluid is supplied to an internal space of the cuff.

3 Claims, 22 Drawing Sheets

(51) Int. Cl.
*A61B 5/0225* (2006.01)
*A61B 5/0235* (2006.01)
*A61B 5/00* (2006.01)
*B29C 65/48* (2006.01)
*B29L 22/02* (2006.01)

(52) U.S. Cl.
CPC .......... *A61B 5/02233* (2013.01); *A61B 5/681* (2013.01); *A61B 5/6832* (2013.01); *A61B 5/742* (2013.01); *A61B 2560/0214* (2013.01); *A61B 2562/0247* (2013.01); *B29C 65/48* (2013.01); *B29L 2022/02* (2013.01)

(58) Field of Classification Search
CPC ................. A61B 5/6832; A61B 5/742; A61B 2560/0214; A61B 2562/0247; A61B 5/6824; A61B 5/022; A61B 2560/0209; A61B 2560/0242; A61B 2560/029; A61B 2560/04; A61B 2562/0204; A61B 2562/12; A61B 5/02116; A61B 5/02225; A61B 5/02241; A61B 5/02438; A61B 5/02444; A61B 5/489; A61B 5/6831; A61B 5/6843; A61B 5/6844; A61B 5/7214; A61B 5/7445; B29C 65/48; B29L 2022/02
USPC ....................................................... 600/492
See application file for complete search history.

(56) References Cited

U.S. PATENT DOCUMENTS

2010/0307673 A1* 12/2010 Matsumoto ........ A61B 5/02233
156/253
2015/0182138 A1* 7/2015 Yoshino .................. B29C 53/40
600/499

FOREIGN PATENT DOCUMENTS

| JP | 2004-195056 A | 7/2004 |
| JP | 2006-158543 A | 6/2006 |
| JP | 2013-220187 A | 10/2013 |
| JP | 2014-033829 A | 2/2014 |

OTHER PUBLICATIONS

Machine Translation of JP2004195056A (Year: 2004).*
Apr. 2, 2019 International Search Report issued in International Patent Application No. PCT/JP2019/000343.
Jul. 21, 2020 International Preliminary Report on Patentability issued in International Patent Application No. PCT/JP2019/000343.
Jul. 20, 2021 Office Action issued in Japanese Patent Application No. 2018-004448.

* cited by examiner

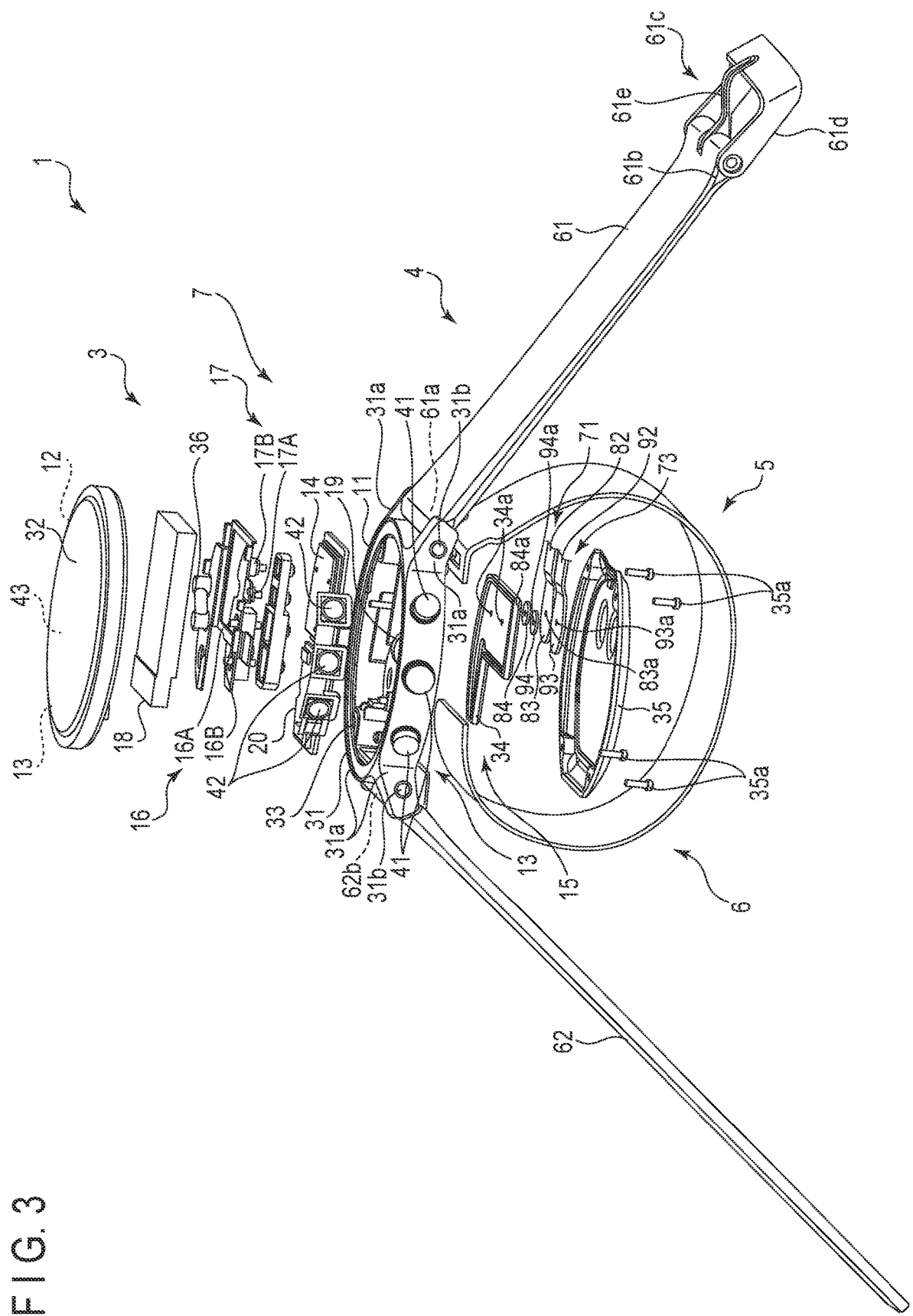
F I G. 3

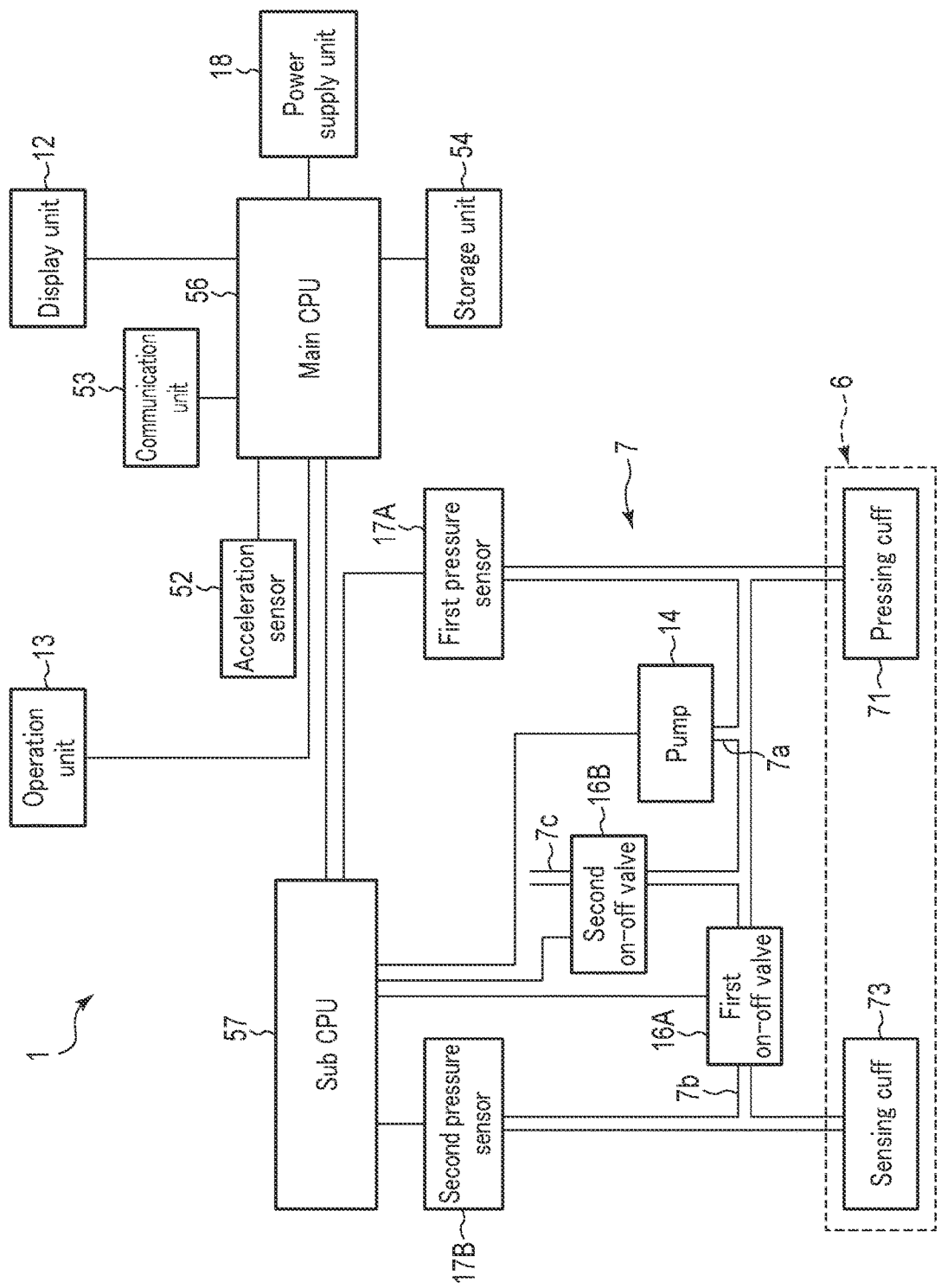
F I G. 4

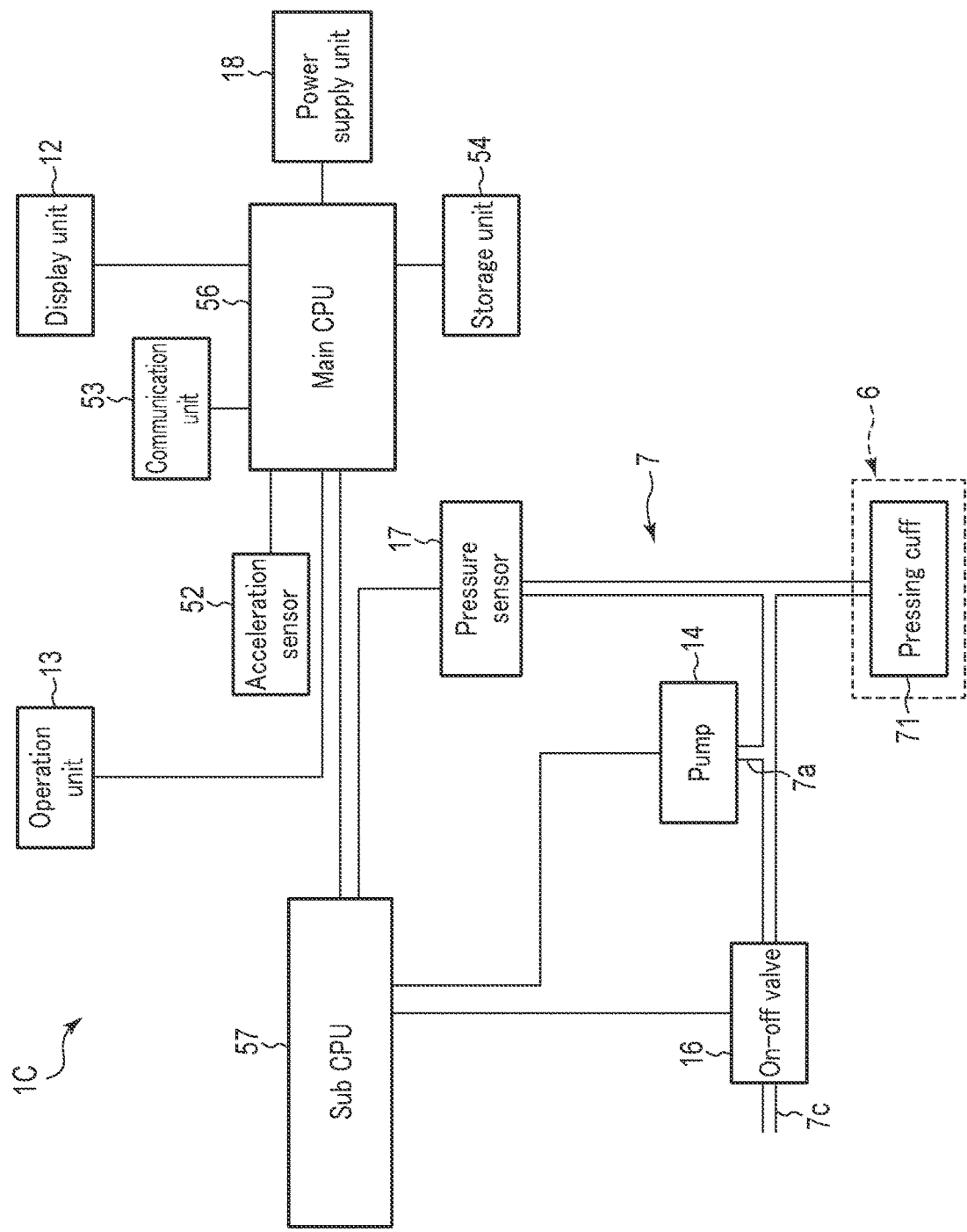
F I G. 25

BLOOD PRESSURE MEASURING DEVICE AND METHOD OF MANUFACTURING BLOOD PRESSURE MEASURING DEVICE

CROSS-REFERENCE TO RELATED APPLICATIONS

This is a Continuation Application of PCT application No. PCT/JP2019/000343, filed Jan. 9, 2019, which was published under PCT Article 21(2) in Japanese.

This application is based upon and claims the benefit of priority from Japanese Patent Application No. 2018-004448, filed Jan. 15, 2018, the entire contents of which are incorporated herein by reference.

FIELD

The present invention relates to a blood pressure measuring device for the measurement of blood pressure and a method of manufacturing the blood pressure measuring device.

BACKGROUND

In recent years, a blood pressure measuring device for the use of blood pressure measurement has been utilized not only in medical facilities but also in households as a means to confirm health condition. A blood pressure measuring device includes, for example: a cuff having an internal space and wound around an upper arm, a wrist, or the like of a living body; and a device main body including a pump that supplies a fluid to the internal space of the cuff and a pressure sensor. A blood pressure measuring device measures blood pressure by detecting vibrations of an arterial wall, by, for example, winding a cuff around an upper arm, a wrist, or the like of a living body, inflating and deflating the cuff, and detecting the pressure of the cuff with the use of a pressure sensor (e.g., Jpn. Pat. Appln. KOKAI Publication No. 2013-220187).

In such a blood pressure measuring device, a device main body and a cuff are connected by a connection structure portion. For the connection structure portion, for example, a nipple having a concave portion is formed around a hole formed in the cuff, and an annular protrusion that engages with the concave portion of the nipple is formed around a nozzle of the device main body. The protrusion of the device main body is inserted into and engaged with the concave portion of the nipple, whereby the device main body and the cuff are connected to each other so that the flow paths communicate with each other. At this time, a seal member such as an O-ring is mounted around the nozzle, thereby fluid-tightly closing the joint portion.

As described above, in the configuration using a connection structure portion having a protrusion, the thickness of the connected part is increased, and the size of the device is increased.

SUMMARY

For such a blood pressure measuring device, a technique that can reduce the thickness of the device is required.

According to one aspect, there is provided a blood pressure measuring device including: a device main body configured to form a flow path of a fluid and supply the fluid; and a cuff to be wound around a living body, the cuff provided with a bag-shaped connection portion with an opening and a connection plate with a hole communicating with the opening, the connection portion formed of a sheet member, the connection plate having a bending elastic modulus higher than that of the connection portion, bonded to the connection portion and adhered to the device main body, and the cuff configured to be inflated when the fluid is supplied to an internal space of the cuff.

Herein, the fluid includes liquid and air. The cuff is wound around an upper arm, a wrist, or the like of a living body when blood pressure is measured, and is inflated by supplying a fluid thereto. For example, the cuff includes a pressing cuff provided in a blood pressure measuring device that measures blood pressure at the wrist, a sensing cuff, and a cuff provided in a blood pressure measuring device that measures blood pressure at the upper arm. The cuff herein may be a bag-shaped structure such as an air bag constituting the pressing cuff. Also herein, the device main body is a supply device of a blood pressure measuring device including a pump and a flow path.

According to this aspect, the connection plate is provided between the cuff and the supply device, the connection plate is bonded to the cuff, and the connection plate is attached to the device main body, whereby the cuff and the device main body can be easily connected. Therefore, the thickness of the connected part can be reduced as compared to a connection structure using a protrusion or the like.

For example, when a cuff having flexibility is inflated, stress is applied to the connected part due to deformation of the cuff, causing the connected part to be easily peeled off. In the blood pressure measuring device according to the above aspect, however, the connection plate having high rigidity is interposed, so that deformation of the connected part can be suppressed and peeling due to the deformation can be suppressed.

In addition, it is possible to perform repair by peeling off the adhered part, achieving a configuration with good maintainability.

There is provided the blood pressure measuring device according to the above aspect, wherein: the cuff includes a pressing cuff and a sensing cuff each including an internal space, and a plurality of the connection portions configured to communicate with the internal space of the pressing cuff and the internal space of the sensing cuff; the connection portion and the connection plate are configured to be bonded to each other around the opening and the hole; and the internal space is configured to communicate with the flow path via the opening and the hole.

According to this aspect, the internal spaces of the pressing cuff and the sensing cuff communicate with the flow path of the device main body, and air leakage can be suppressed.

There is provided the blood pressure measuring device according to the above aspect, wherein the device main body includes a base with a flow path section, a pump disposed on one side of the base, a flow path cover disposed to face another side of the base to cover the flow path section, and a back cover disposed on another side of the flow path cover; and the connection plate is formed in a plate shape and disposed between the flow path cover and the back cover, one surface of the connection plate is adhered to the flow path cover, and another surface of the connection plate is bonded to the connection portion of the cuff.

According to this aspect, by peeling off the adhered part between the flow path cover and the connection plate, the connection plate can be individually peeled off and repaired with the flow path cover covering the base, thus achieving high level of maintainability.

There is provided the blood pressure measuring device according to the above aspect, wherein: the device main body includes a base with a flow path section, a pump disposed on one side of the base, and a back cover disposed on another side of the base; and the connection plate is a flow path cover disposed to face another side of the base to cover the flow path section and is configured to be adhered to the base.

According to this aspect, since the connection plate is formed as the flow path cover, the number of components can be reduced, and the manufacturing process can be simplified. Also, it is possible to remove the flow path cover from the base and repair the flow path cover, thus achieving high level of maintainability.

There is provided the blood pressure measuring device according to the above aspect, wherein: the flow path cover includes a base plate, a first adhesive layer disposed on one side of the base plate, and a second adhesive layer disposed on another side of the base plate; and the connection plate is attached to the second adhesive layer.

According to this aspect, the connection plate can be easily attached to the flow path cover.

According to one aspect, there is provided a method of manufacturing a blood pressure measuring device, the method including: bonding a connection plate with a hole to a bag-shaped connection portion with an opening, the hole communicating with the opening, the connection plate having a bending elastic modulus higher than that of the connection portion, the connection portion formed of a sheet member and configured to be inflated when a fluid is supplied to an internal space of the connection portion; and adhering the connection plate to a device main body configured to form a flow path of the fluid and supply the fluid.

According to this aspect, the cuff and the device main body can be easily connected. Therefore, reduction of the thickness of the connected part can be achieved as compared to a connection structure using a protrusion or the like.

The present invention can provide a blood pressure measuring device that can be made thinner and a method of manufacturing the blood pressure measuring device.

BRIEF DESCRIPTION OF THE DRAWINGS

FIG. 3 is an exploded view of a configuration of the blood pressure measuring device.

FIG. 4 is a block diagram showing a configuration of the blood pressure measuring device.

FIG. 25 is a block diagram showing a configuration of the blood pressure measuring device.

DETAILED DESCRIPTION

First Embodiment

Hereinafter, an example of a blood pressure measuring device 1 according to a first embodiment of the present invention will be described with reference to FIGS. 1 to 12.

Figure 1:
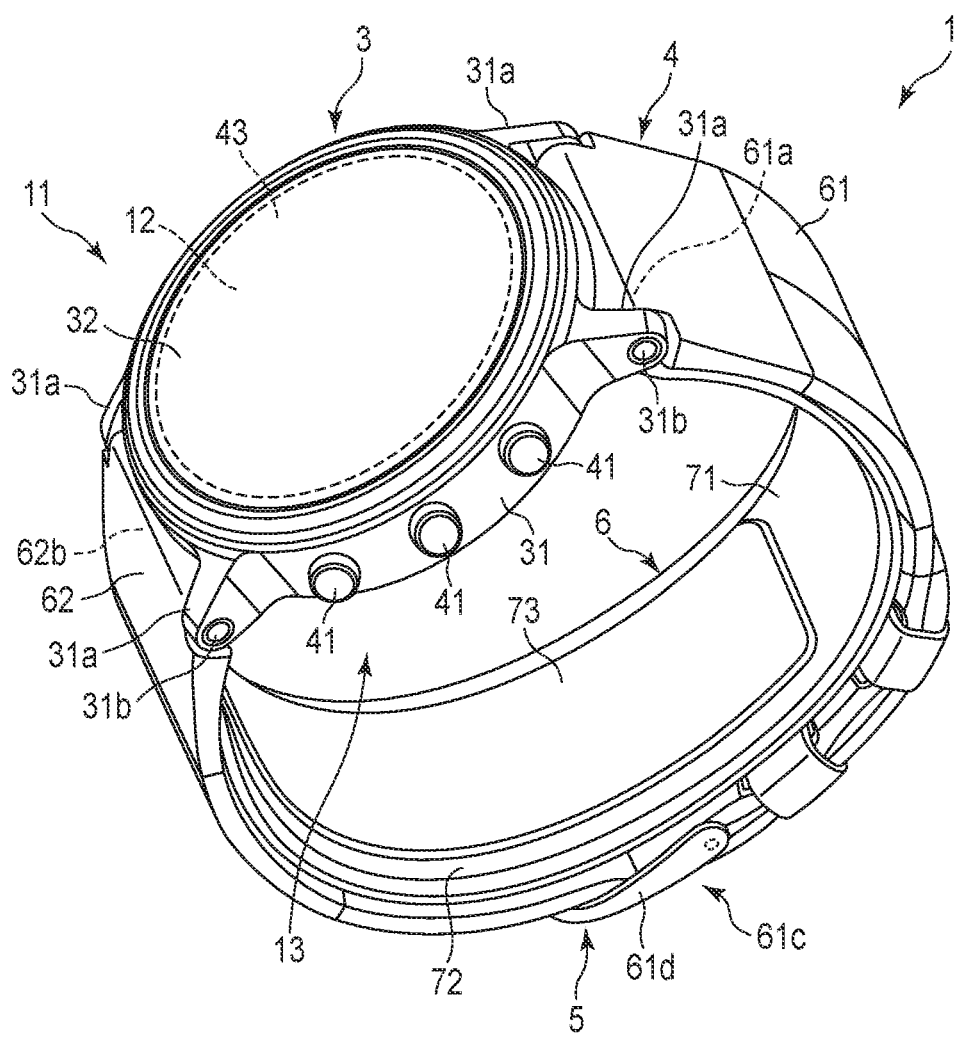
FIG. 1 is a perspective view of a configuration of a blood pressure measuring device according to a first embodiment of the present invention.
Figure 2:
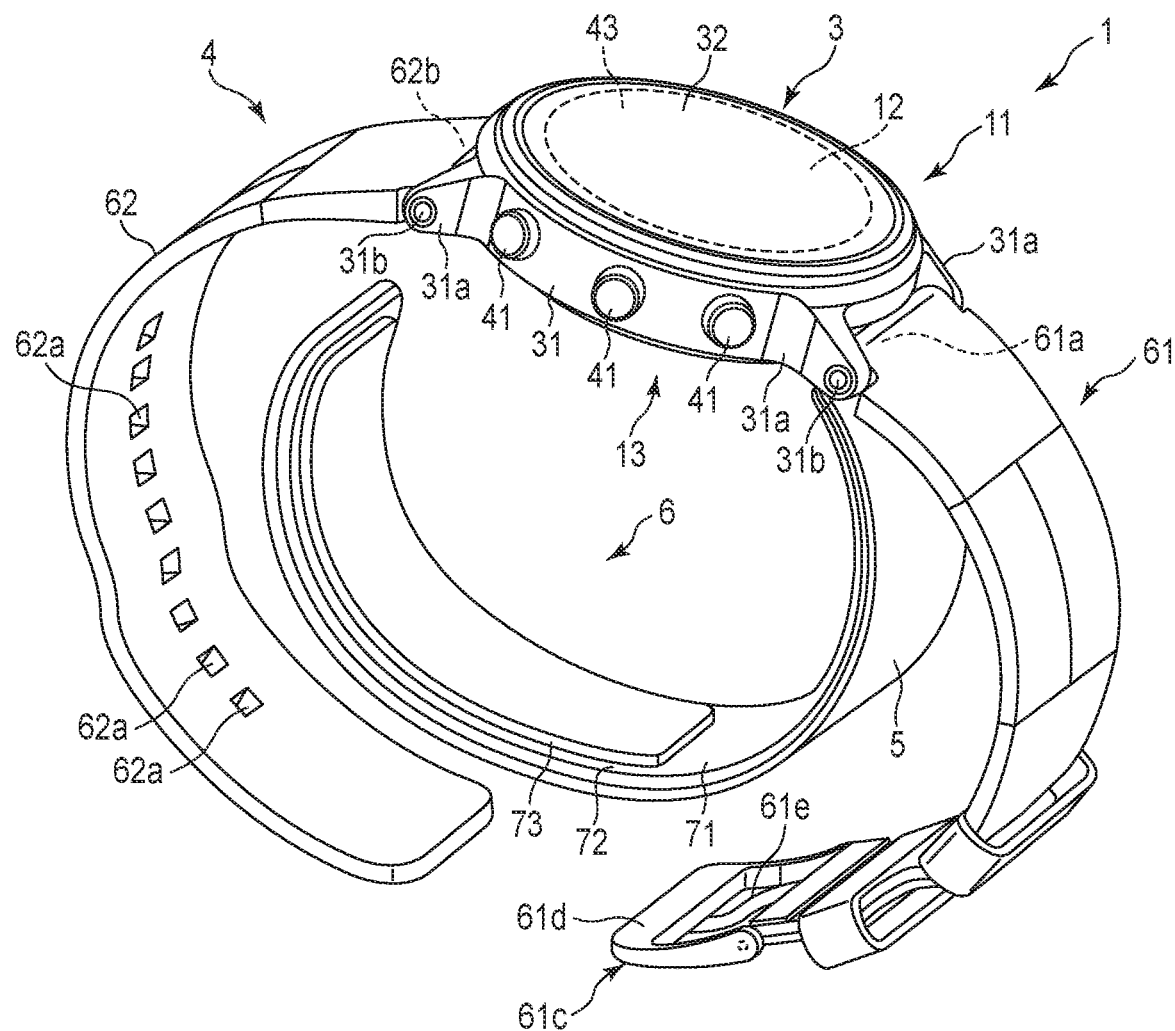
FIG. 2 is a perspective view of a configuration of the blood pressure measuring device.
Figure 5:
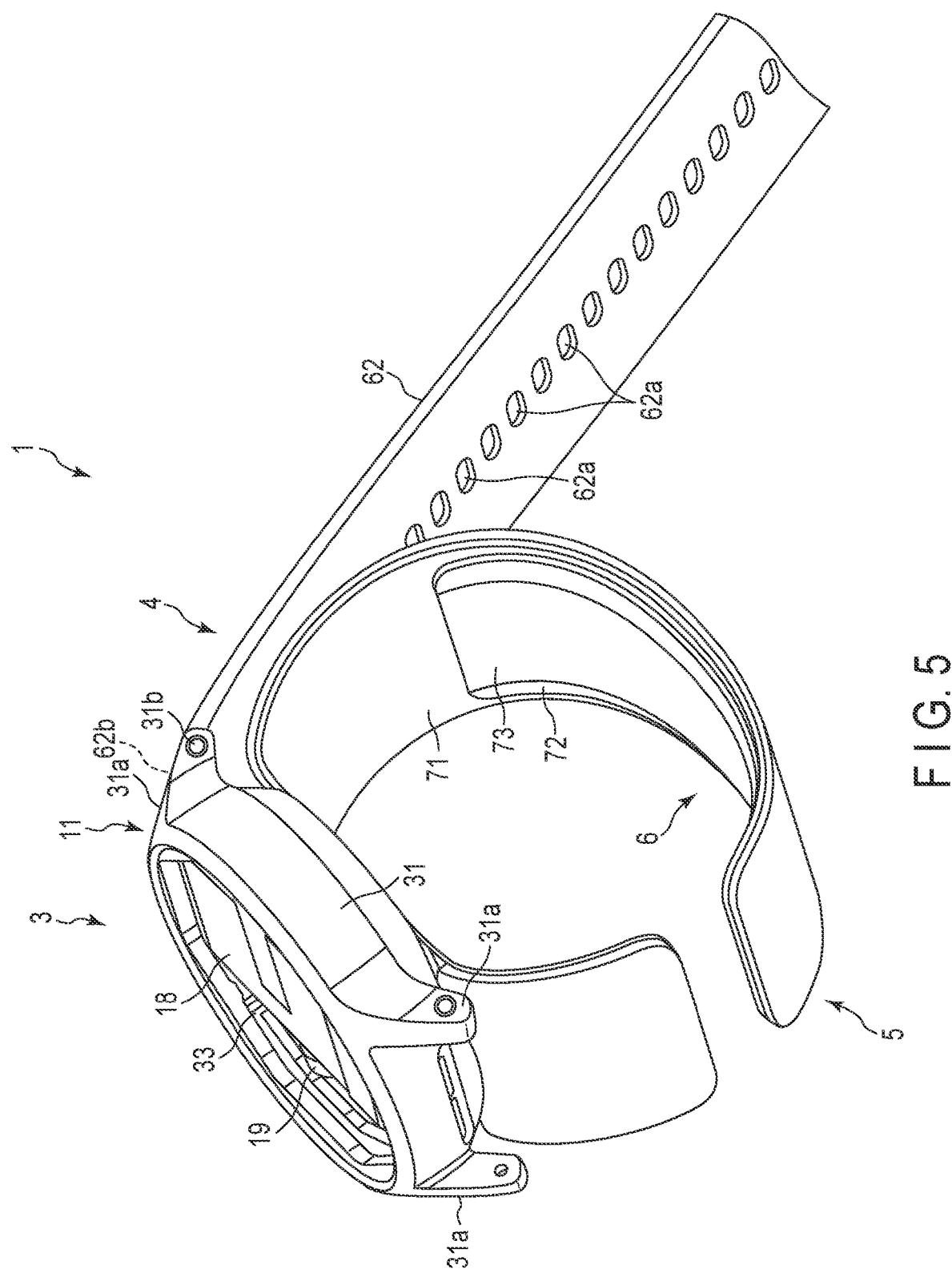
FIG. 5 is a perspective view of another configuration of the blood pressure measuring device.
Figure 6:
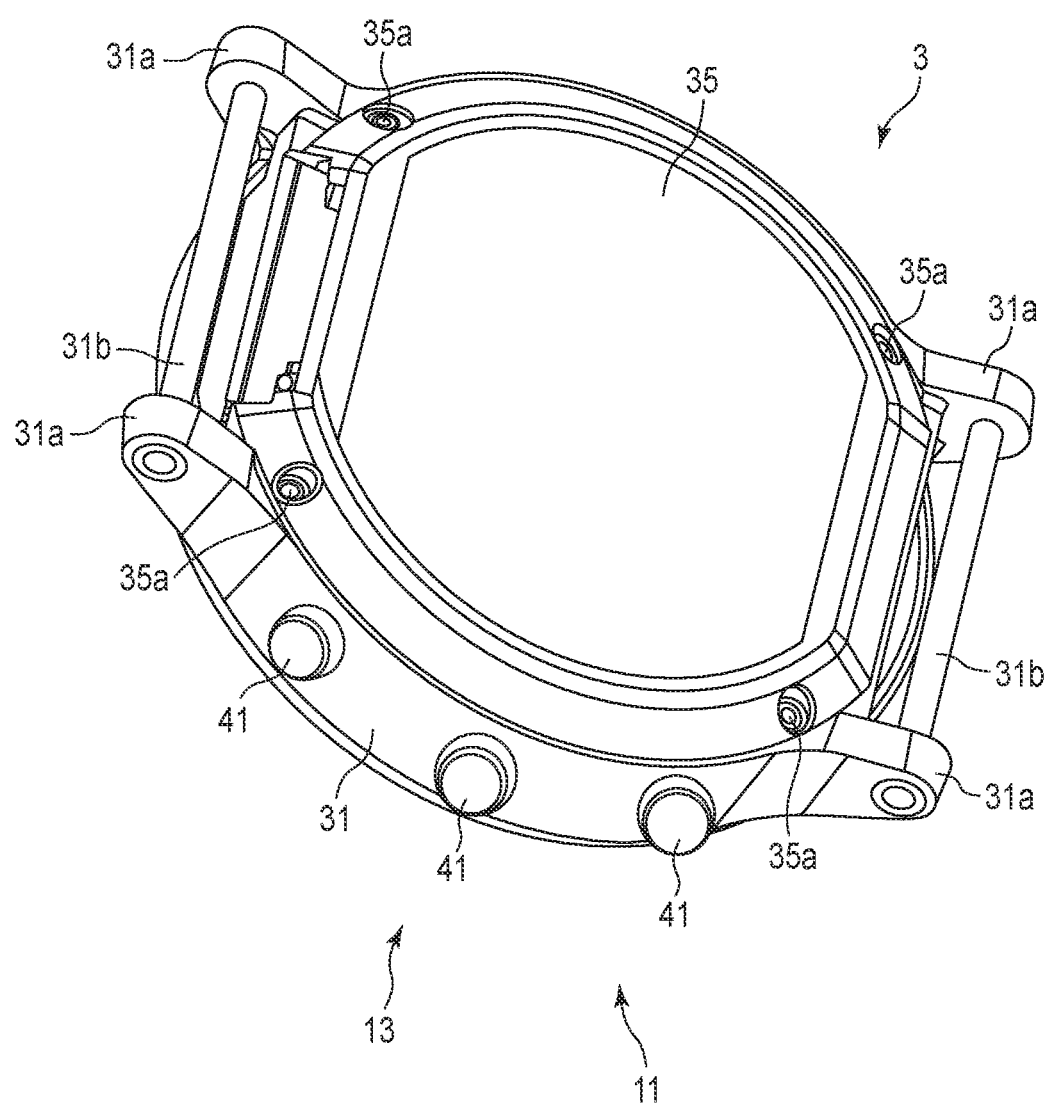
FIG. 6 is a perspective view of a configuration of a device main body of the blood pressure measuring device.
Figure 7:
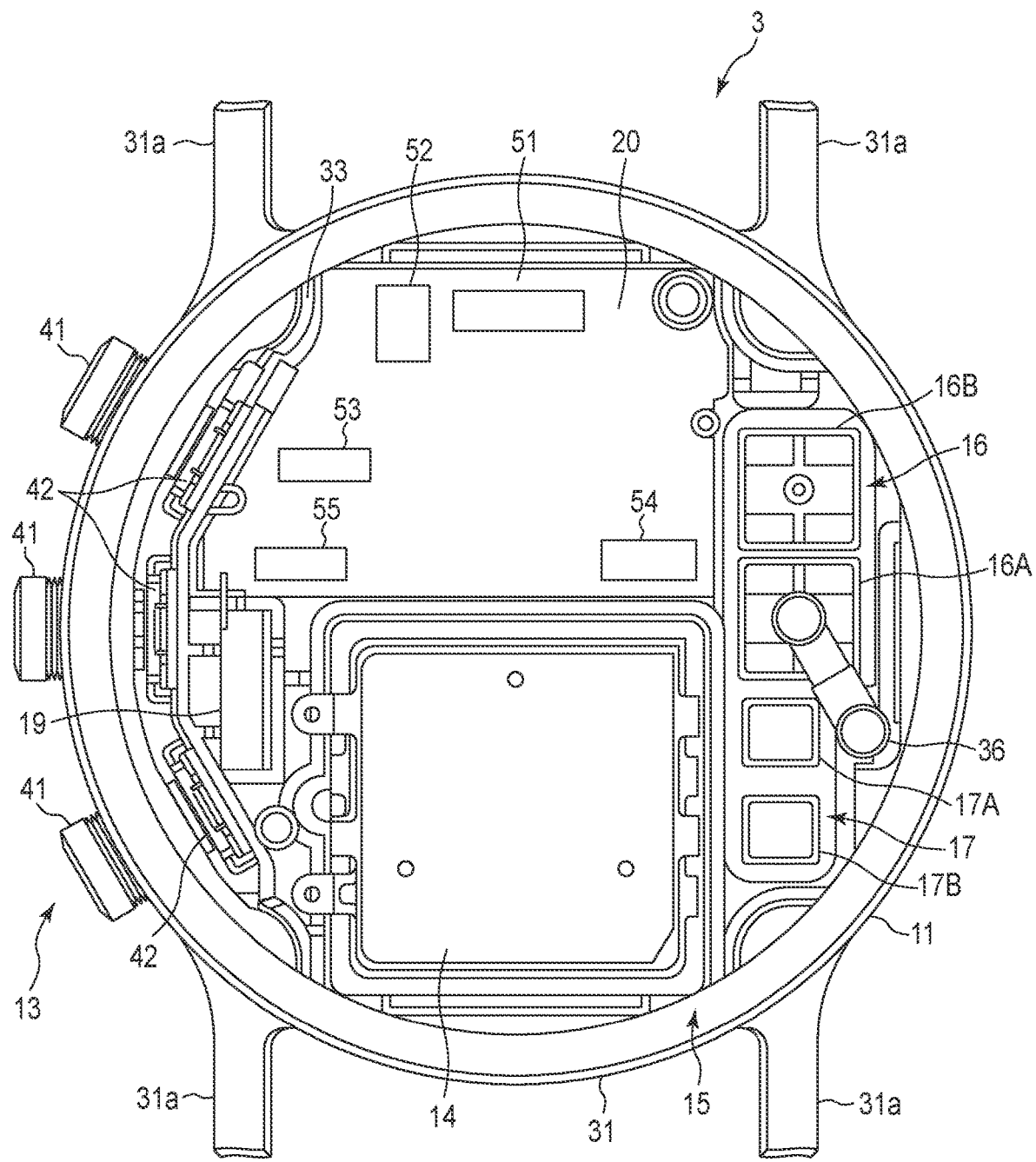
FIG. 7 is a plan view of an internal configuration of the device main body.
Figure 8:
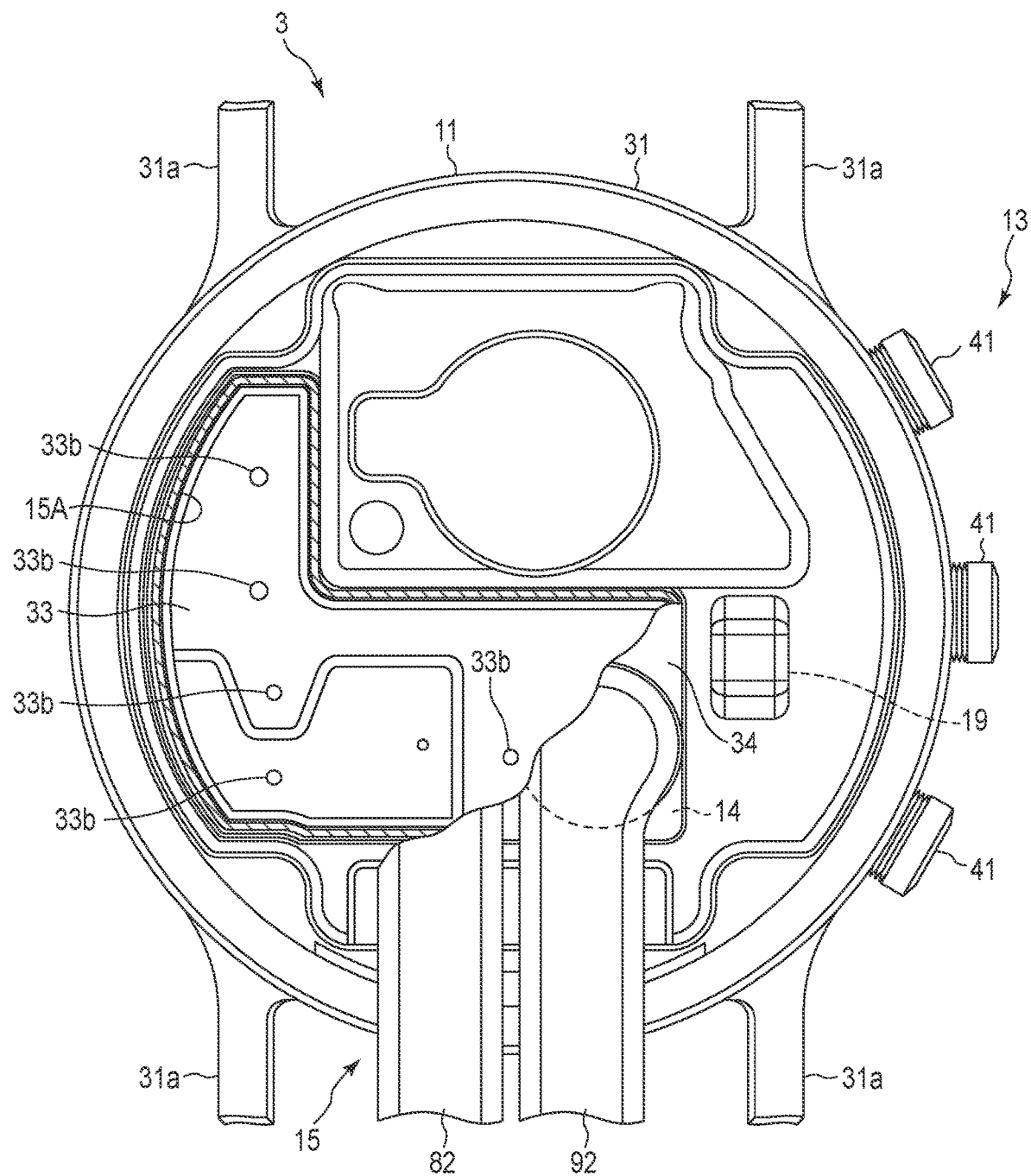
FIG. 8 is a plan view of an internal configuration of the device main body.
Figure 9:
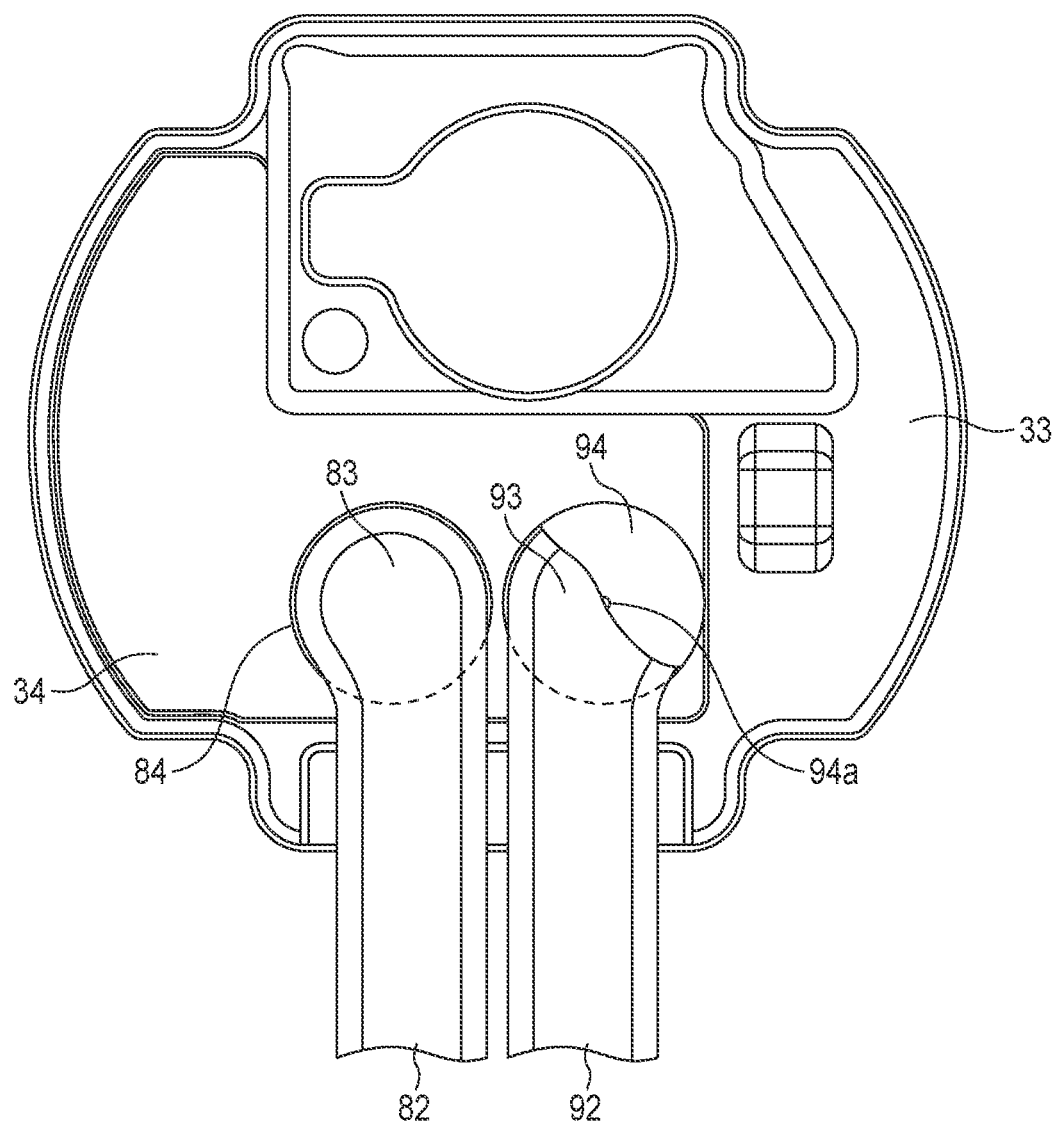
FIG. 9 is a plan view of an internal configuration of the device main body.
Figure 10:
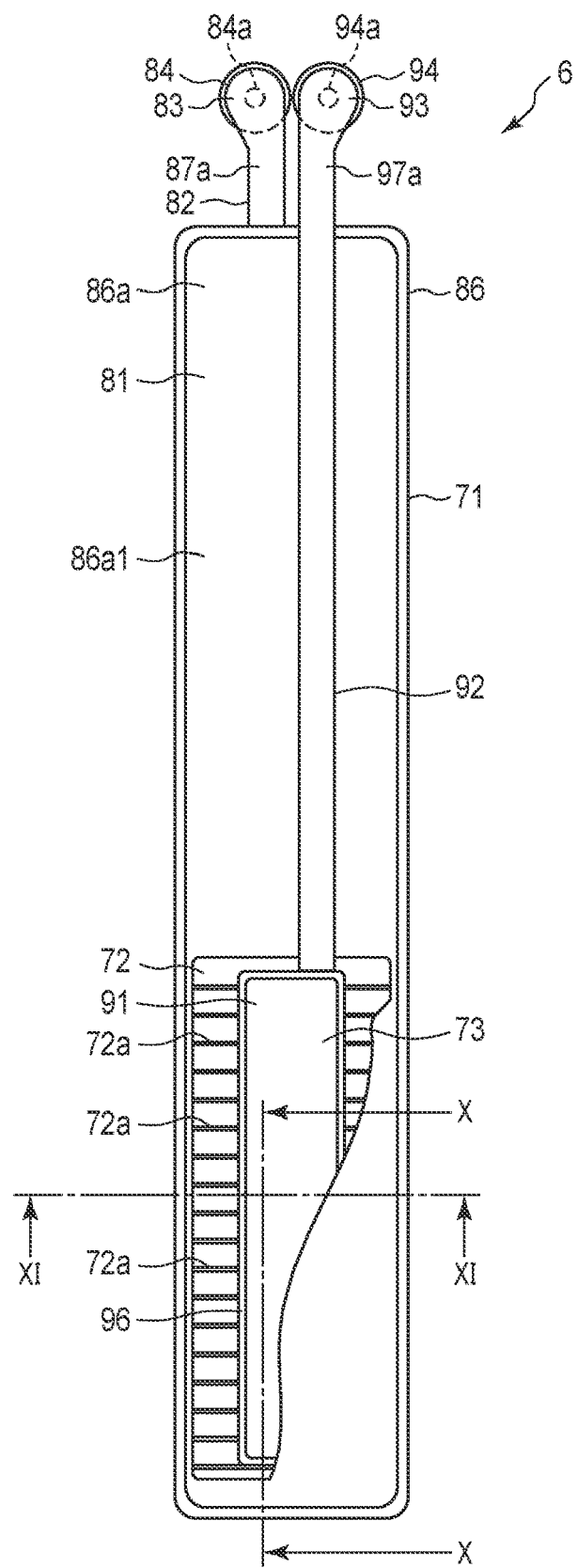
FIG. 10 is a plan view of a configuration of a cuff structure of the blood pressure measuring device.
Figure 11:
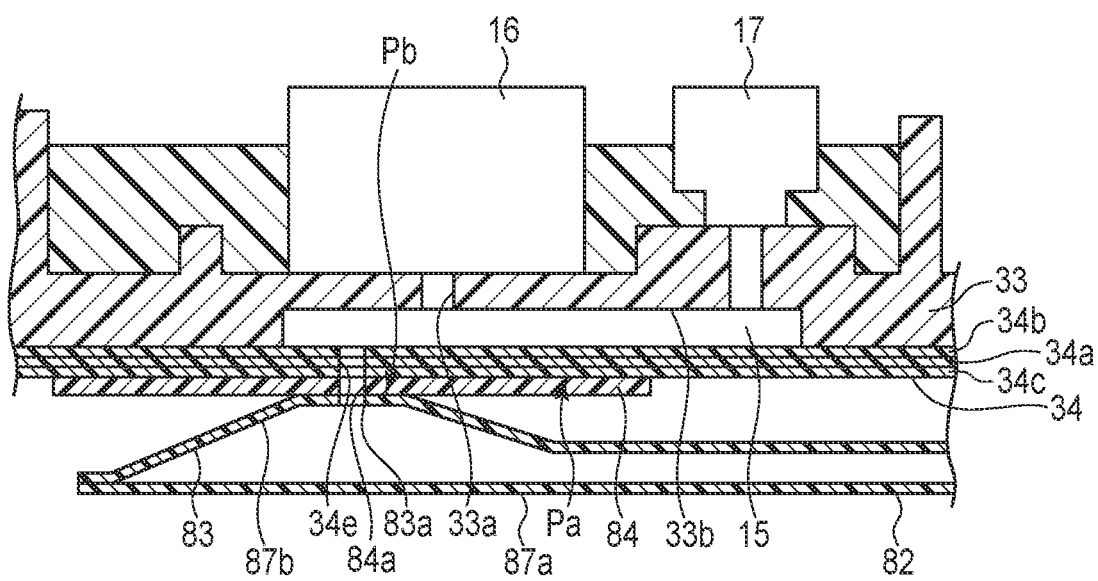
FIG. 11 is a cross-sectional view of a configuration of a connection portion between the device main body and the cuff structure of the blood pressure measuring device.

FIG. 1 is a perspective view of a configuration of the blood pressure measuring device 1 according to the first embodiment of the present invention with a belt 4 closed. FIG. 2 is a perspective view of a configuration of the blood pressure measuring device 1 with the belt 4 opened. FIG. 3 is an exploded view of a configuration of the blood pressure measuring device 1. FIG. 4 is a block diagram showing a configuration of the blood pressure measuring device 1. FIG. 5 is a perspective view of a configuration of the blood pressure measuring device 1. FIG. 6 is a perspective view of a configuration of a device main body 3 of the blood pressure measuring device 1, as viewed from a back cover 35 side. FIGS. 7 and 8 are plan views of an internal configuration of the device main body 3, as viewed from a windshield 32 side and the back cover 35 side, respectively. In FIG. 8, a flow path cover 34 and a cuff structure 6 are partially cut away to show the internal structure. FIG. 9 is a plan view of an internal configuration of the device main body 3, as viewed from the back cover 35 side. In FIG. 9, the cuff structure 6 is partially cut away to show the internal structure. FIG. 10 is a plan view of a configuration of the cuff structure 6 of the blood pressure measuring device 1, as viewed from a sensing cuff 73 side. FIG. 11 is a cross-sectional view of a connection portion between the device main body 3 and the cuff structure 6.

Figure 12:
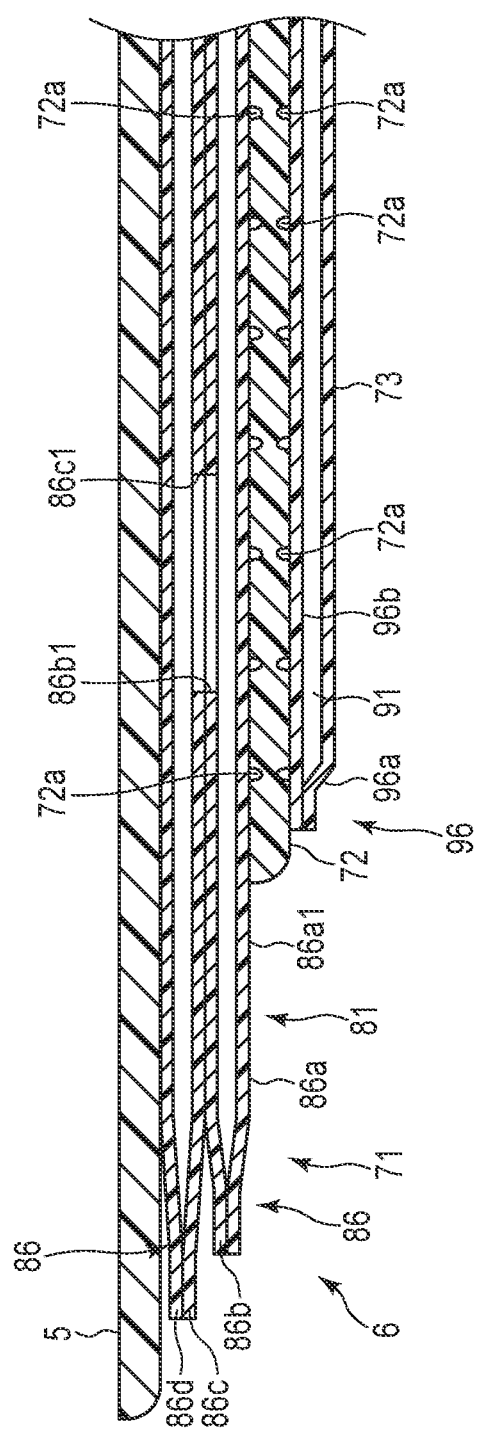
FIG. 12 is a cross-sectional view of configurations of a curler and the cuff structure of the blood pressure measuring device.
Figure 13:
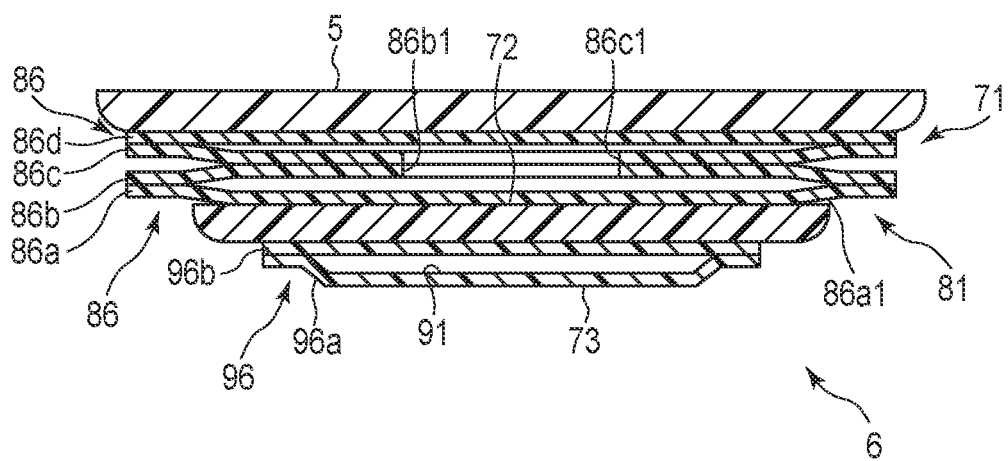
FIG. 13 is a cross-sectional view of configurations of the curler and the cuff structure.
Figure 14:
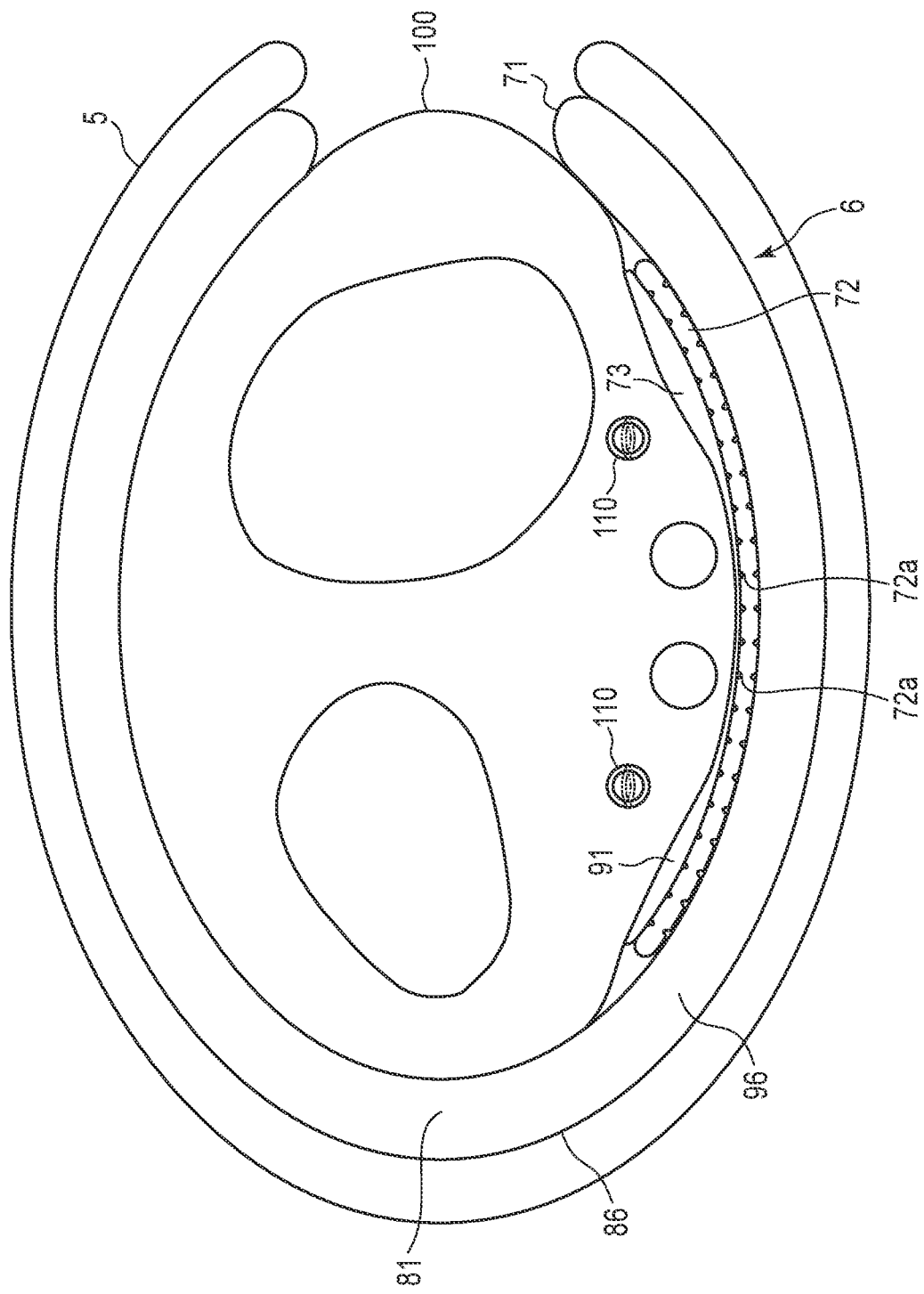
FIG. 14 is a side view schematically showing a configuration of the cuff structure in which a pressing cuff is inflated.
Figure 15:
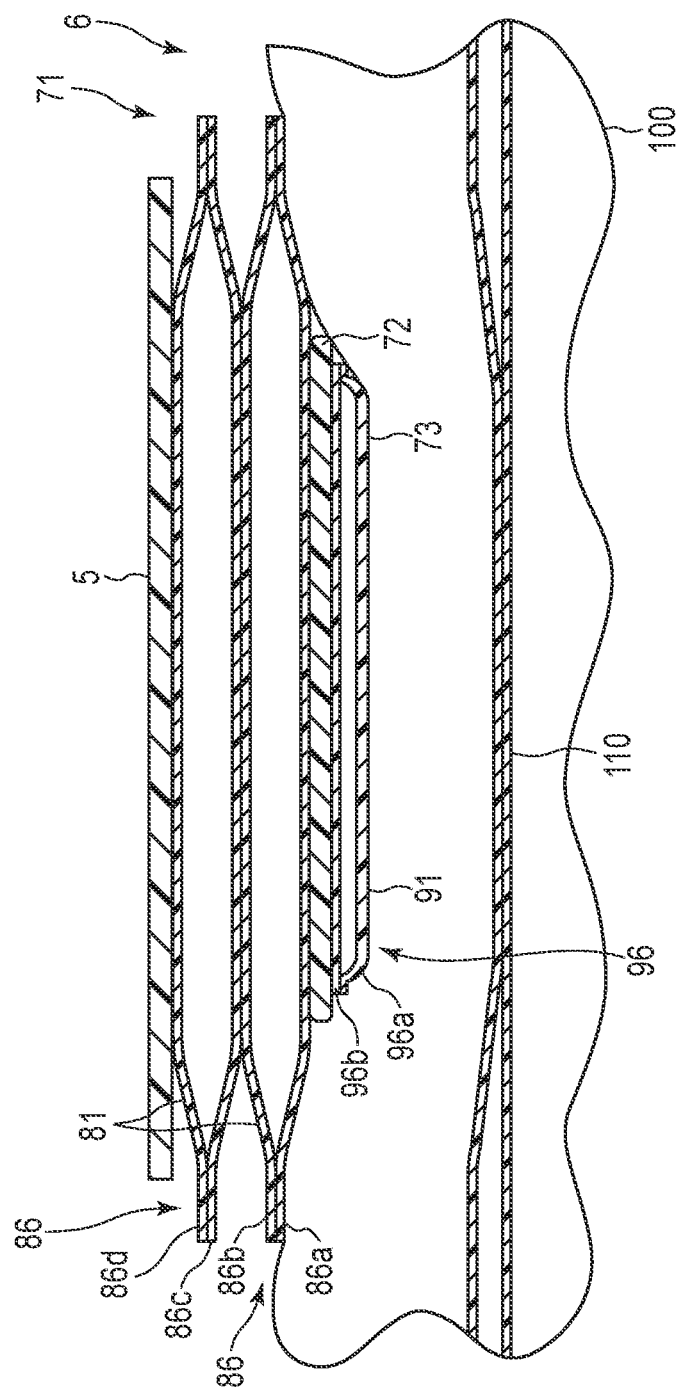
FIG. 15 is a cross-sectional diagram schematically showing a configuration of the cuff structure in which the pressing cuff is inflated.

FIG. 12 is a cross-sectional diagram schematically showing configurations of a curler 5 and the cuff structure 6 of the blood pressure measuring device 1 taken along line X-X in FIG. 10. FIG. 13 is a cross-sectional view of configurations of the curler 5 and the cuff structure 6, taken along line XI-XI in FIG. 10. FIGS. 14 and 15 are side and sectional views schematically showing an example of the cuff structure 6 in which a pressing cuff 71 and the sensing cuff 73 are inflated. In FIG. 12, the curler 5 and the cuff structure 6 are schematically shown in a linear shape for convenience of explanation; however, these components are in a bent shape when provided in the blood pressure measuring device 1.

The blood pressure measuring device 1 is an electronic blood pressure measuring device worn on a living body. In the present embodiment, an electronic blood pressure measuring device in the form of a wearable device worn on a wrist 100 of a living body will be described. As shown in FIGS. 1 to 15, the blood pressure measuring device 1 includes: the device main body 3; the belt 4; the curler 5; the cuff structure 6 with the pressing cuff 71 and the sensing cuff 73; and a fluid circuit 7. In the present embodiment, the pressing cuff 71 is an example of the □cuff□ of the present invention.

As shown in FIGS. 1 to 8, the device main body 3 includes a case 11, a display 12, an operation unit 13, a pump 14, a flow path section 15, an on-off valve 16, a pressure sensor 17, a power supply unit 18, a vibration motor 19, and a control substrate 20. The device main body 3 is a supply device that supplies a fluid to the pressing cuff 71 by using the pump 14, the on-off valve 16, the pressure sensor 17, the control substrate 20, and the like.

The case 11 includes an outer case 31; a windshield 32 that covers an upper opening of the outer case 31; a base 33 provided in a lower part of the inside of the outer case 31; a flow path cover 34 that covers a part of a back surface of the base 33; and a back cover 35 that covers a lower side of the outer case 31. The case 11 also includes a flow path tube 36 forming a part of the fluid circuit 7.

The outer case 31 is formed in a cylindrical shape. The outer case 31 includes: pairs of lugs 31a provided at symmetrical positions in the circumferential direction of the outer peripheral surface; and spring bars 31b respectively provided between the paired lugs 31a. The windshield 32 is a circular glass plate.

The base 33 is provided in a lower part of the outer case 31 and is formed in a disk shape. The base 33 holds, on one of the main surface sides of the base 33, the display 12, the operation unit 13, the pump 14, the on-off valve 16, the pressure sensor 17, the power supply unit 18, the vibration motor 19, and the control substrate 20. The base 33 forms a part of the flow path section 15 on the other main surface side of the base 33.

A hole 33a, as a through hole, is formed in a position of the base 33 facing the pump 14. On one side of the base 33, that is, on the windshield 32 side, components such as the pump 14, the on-off valve 16, and the pressure sensor 17 are sealed with, for example, a hot-melt resin or an adhesive material. A groove 33b forming a part of the flow path section 15 is formed on the other side of the base 33, that is, on the surface of the base 33 on the back cover 35 side.

The flow path cover 34 is fixed to a back surface of the base 33, which is on the back cover 35 side. A groove is provided in one or both of the base 33 and the flow path cover 34, thereby forming a part of the flow path section 15. A pair of holes 34e, as through holes for enabling the flow path section 15 to communicate with the internal space of the cuff, are formed at predetermined positions of the flow path cover 34.

The flow path cover 34 includes a base plate 34a, a first adhesive layer 34b provided on one surface of the base plate 34a, and a second adhesive layer 34c provided on the other surface of the base plate 34a, which are stacked on top of each other.

The base plate 34a may be made of a material having high rigidity, and the material is selected from resins, metals, ceramics, and the like. For example, the base plate 34a is a metallic plate having a thickness of about 0.1 mm and is formed of a stainless-steel plate. The surface of the base plate 34a is flat. The adhesive layers 34b and 34c are double-sided adhesive tape each having a thickness of about 0.1 mm. For example, the adhesive layers 34b and 34c may be applied to the base 33 or to a connection plate 84. Also, the adhesive layers are not limited to double-sided adhesive tape, and an adhesive or the like may be used.

The pressing cuff 71 and the sensing cuff 73 are respectively bonded to a region that is on a surface of the second adhesive layer 34c on the back cover side and includes the hole 34e.

The back cover 35 covers an end of the outer case 31 on the living body side. The back cover 35 is fixed to an end of the outer case 31 or the base 33 on the living body side by, for example, four screws 35a or the like.

The flow path tube 36 forms a part of the flow path section 15. The flow path tube 36 connects, for example, the on-off valve 16 and a part of the base 33 forming the flow path section 15.

The display 12 is disposed on the base 33 of the outer case 31 and directly below the windshield 32. The display 12 is electrically connected to the control substrate 20. The display 12 is, for example, a liquid crystal display or an organic electroluminescence display. The display 12 displays various kinds of information including date and time, and measurement results of blood pressure values, such as systolic blood pressure and diastolic blood pressure, a heart rate, and the like.

The operation unit 13 is configured to allow a user to input a command. For example, the operation unit 13 includes: a plurality of buttons 41 provided to the case 11; a sensor 42 that detects an operation of the buttons 41; and a touch panel 43 provided to the display 12 or the windshield 32. The operation unit 13 is operated by a user to convert a command into an electric signal. The sensor 42 and the touch panel 43 are electrically connected to the control substrate 20 and output an electric signal to the control substrate 20.

For example, three buttons 41 are provided. The buttons 41 are supported by the base 33 and protrude from the outer peripheral surface of the outer case 31. The plurality of buttons 41 and the plurality of sensors 42 are supported by the base 33. For example, the touch panel 43 is provided integrally to the windshield 32.

The pump 14 is, for example, a piezoelectric pump. The pump 14 compresses the air and supplies the compressed air to the cuff structure 6 via the flow path section 15. The pump 14 is electrically connected to the controller 55.

The flow path section 15 is an air flow path formed of a groove or the like provided in the flow path cover 34 that covers the back cover 35 side of the base 33 and the main surface of the base 33 on the back cover 35 side. The flow path section 15 forms a flow path leading from the pump 14 to the pressing cuff 71, and a flow path leading from the pump 14 to the sensing cuff 73. The flow path section 15 also forms a flow path leading from the pressing cuff 71 to the atmosphere, and a flow path leading from the sensing cuff 73 to the atmosphere.

The on-off valve 16 opens and closes a part of the flow path section 15. For example, a plurality of on-off valves 16 are provided, and selectively open and close the flow path leading from the pump 14 to the pressing cuff 71; the flow path leading from the pump 14 to the sensing cuff 73; the flow path leading from the pressing cuff 71 to the atmosphere; and the flow path leading from the sensing cuff 73 to the atmosphere, depending on the combination of the opening and closing of the on-off valves 16. For example, two on-off valves 16 are used.

The pressure sensor 17 detects the pressure of the pressing cuff 71 and the sensing cuff 73. The pressure sensor 17 is electrically connected to the control substrate 20. The pressure sensor 17 is electrically connected to the control substrate 20, converts the detected pressure into an electric signal, and outputs the electric signal to the control substrate 20. For example, the pressure sensor 17 is provided in the flow path leading from the pump 14 to the pressing cuff 71 and the flow path leading from the pump 14 to the sensing cuff 73. Since these flow paths are continuous with the pressing cuff 71 and the sensing cuff 73, the pressures in these flow paths become the pressures in the internal spaces of the pressing cuff 71 and the sensing cuff 73.

The power supply unit 18 is, for example, a secondary battery such as a lithium ion battery. The power supply unit 18 is electrically connected to the control substrate 20. The power supply unit 18 supplies power to the control substrate 20.

As shown in FIGS. 4 and 7, the control substrate 20 includes, for example, a substrate 51, an acceleration sensor 52, a communication unit 53, a storage 54, and a controller 55. The control substrate 20 is configured by mounting the acceleration sensor 52, the communication unit 53, the storage 54, and the controller 55 on the substrate 51.

The substrate 51 is fixed to the base 33 of the case 11 by a screw or the like.

The acceleration sensor 52 is, for example, a three-axis acceleration sensor. The acceleration sensor 52 outputs, to the controller 55, acceleration signals representing accelerations of the device main body 3 in three directions that are orthogonal to one another. For example, the acceleration sensor 52 is used to measure the amount of activity of the living body wearing the blood pressure measuring device 1 based on the detected accelerations.

The communication unit 53 is configured to be able to transmit and receive information to and from an external device in a wireless or wired manner. For example, the communication unit 53 transmits information controlled by the controller 55 and information such as measured blood pressure values, pulse, and the like to an external device via a network, and receives a program for software update, etc., from the external device via the network to transmit the program, etc., to the controller.

In the present embodiment, the network is, for example, the Internet, but is not limited thereto. The network may be a network such as a local area network (LAN) provided in a hospital, or direct communication with an external device using, for example, a cable having a terminal of a predetermined standard such as a USB may be adopted. Therefore, the communication unit 53 may include a plurality of wireless antennas, micro USB connectors, and the like.

The storage 54 stores in advance program data for controlling the entire blood pressure measuring device 1 and the fluid circuit 7, setting data for the setting of various functions of the blood pressure measuring device 1, calculation data for the calculation of blood pressure values and a pulse from a pressure measured by the pressure sensor 17, and the like. The storage 54 also stores information such as measured blood pressure values and pulse.

The controller 55 is formed of one or more CPUs, and controls the operation of the entire blood pressure measuring device 1 and the operation of the fluid circuit 7. The controller 55 is electrically connected to the display 12, the operation unit 13, the pump 14, the on-off valves 16, and the pressure sensors 17, and supplies electric power. Also, the controller 55 controls the operations of the display 12, the pump 14, and the on-off valves 16 based on the electric signals output from the operation unit 13 and the pressure sensor 17.

For example, the controller 55 includes a main CPU 56 that controls the operation of the entire blood pressure measuring device 1 and a subordinate CPU 57 that controls the operation of the fluid circuit 7, as shown in FIG. 4. For example, when a command to measure blood pressure is input from the operation unit 13, the subordinate CPU 57 drives the pump 14 and the on-off valves 16 to send compressed air to the pressing cuff 71 and the sensing cuff 73.

The subordinate CPU 57 also controls the driving and stoppage of the pump 14 and the opening and closing of the on-off valves 16 based on the electric signal output from the pressure sensor 17, selectively sends compressed air to the pressing cuff 71 and the sensing cuff 73, and selectively pressurizes the pressing cuff 71 and the sensing cuff 73. The main CPU 56 obtains measurement results of blood pressure values, such as systolic blood pressure and diastolic blood pressure, a heart rate, and the like from the electric signal output from the pressure sensor 17, and outputs an image signal corresponding to the measurement results to the display 12.

As shown in FIGS. 1 to 3, the belt 4 includes a first belt 61 provided to one of the pairs of lugs 31a and the spring bar 31b, and a second belt 62 provided to the other pair of lugs 31a and the spring bar 31b.

The first belt 61 is a so-called □parent□ and is formed in a band shape. The first belt 61 includes a first hole 61a provided at one end of the first belt 61 and perpendicular to the longitudinal direction of the first belt 61, a second hole 61b provided at the other end of the first belt 61 and perpendicular to the longitudinal direction of the first belt 61, and a buckle 61c provided in the second hole 61b. The first hole 61a has an inner diameter so that the spring bar 31b can be inserted thereinto and the first belt 61 can rotate with respect to the spring bar 31b. That is, the first hole 61a is disposed between the paired lugs 31a and at the spring bar 31b, so that the first belt 61 is rotatably held by the outer case 31.

The second hole 61b is provided at a distal end of the first belt 61.

The buckle 61c includes a rectangular frame-shaped body 61d and a prodding stick 61e rotatably attached to the frame-shaped body 61d. One side of the frame-shaped body 61d to which the prodding stick 61e is attached is inserted into the second hole 61b, so that the frame-shaped body 61d is rotatably attached with respect to the first belt 61.

The second belt 62 is a so-called □pointed end□ and is formed in a band shape having a width that allows the second belt 62 to be inserted into the frame-shaped body 61d. The second belt 62 includes a plurality of small holes 62a into which the prodding stick 61e is inserted. The second belt 62 also includes a third hole 62b provided at one end of the second belt 62 and perpendicular to the longitudinal direction of the second belt 62. The third hole 62b has an inner diameter so that the spring bar 31b can be inserted thereinto and that the second belt 62 can rotate with respect to the spring bar 31b. That is, the third hole 62b is disposed between the paired lugs 31a and at the spring bar 31b, so that the second belt 62 is rotatably held by the outer case 31.

The belt 4 described above forms an annular shape along the circumferential direction of the wrist 100 together with the outer case 31 as the second belt 62 is inserted into the frame-shaped body 61d and the prodding stick 61e is inserted into the small hole 62a, thereby integrally connecting the first belt 61 and the second belt 62 to each other.

The curler 5 is made of a resin material and has a band shape bent along the circumferential direction of the wrist. For example, one end of the curler 5 is fixed between the back cover 35 and the base 33 as well as the flow path cover 34 of the device main body 3, and the other end of the curler 5 is close to the device main body 3. As shown in FIG. 5, the curler 5 may be configured so that the curler 5 is fixed to the outer surface of the back cover 35, that one end of the curler 5 protrudes from a side of the back cover 35 closer to one of the pairs of lugs 31a, and that the other end of the curler 5 protrudes from a side of the back cover 35 closer to the other pair of lugs 31a and extends to a position adjacent to one end of the curler 5.

As shown in FIGS. 1 to 3 and FIG. 12, the curler 5 is made of a resin material having a shape bent along the circumferential direction of the wrist 100, for example, in a side view from a direction perpendicular to the circumferential direction of the wrist, in other words, the longitudinal direction of the wrist. For example, the curler 5 extends from the device main body to the palmar side through the dorsal side of the wrist and one side of the wrist, and extends toward the center of the other side of the wrist. That is, the curler 5 bends along the circumferential direction of the wrist and thereby extends over most parts of the wrist 100 in the circumferential direction of the wrist 100, and both ends of the curler 5 are separated from each other by a predetermined interval.

The curler 5 has a hardness encompassing both flexibility and shape-retaining capability. The □flexibility□ means that the curler 5 deforms in the radial direction when an external force is applied to the curler 5, and means that when the curler 5 is pressed by the belt 4, for example, the curler 5 deforms so as to approach the wrist, conform to the shape of the wrist, or trace the shape of the wrist, as viewed from a side of the curler 5. The □shape-retaining capability□ means that the curler 5 can maintain a pre-formed shape when no external force is applied thereto; and in the present embodiment, it means that the curler 5 can maintain a shape bent along the circumferential direction of the wrist. The curler 5 is made of a resin material. For example, the curler 5 is made of polypropylene and has a thickness of about 1 mm. The curler 5 holds the cuff structure 6 along the inner surface shape of the curler 5.

As shown in FIGS. 1 to 5 and 12 to 14, the cuff structure 6 includes the pressing cuff 71, the back plate 72, and the sensing cuff 73. The cuff structure 6 is configured so that the pressing cuff 71, the back plate 72, and the sensing cuff 73 are stacked and integrally formed. The cuff structure 6 is fixed to the inner surface of the curler 5.

The pressing cuff 71 is an example of the cuff. The pressing cuff 71 is fluidly connected to the pump 14 via the flow path section 15. The pressing cuff 71 is inflated to press the back plate 72 and the sensing cuff 73 toward the living body. The pressing cuff 71 includes a plurality of air bags 81, a tube 82 communicating with the air bags 81, and a connection portion 83 provided at a distal end of the tube 82.

The air bag 81 is a bag-shaped structure. Since the blood pressure measuring device 1 is configured to use the air with the pump 14 in the present embodiment, an air bag will be described. However, when a fluid other than the air is used, the bag-shaped structure may be a fluid bag such as a liquid bag.

The plurality of air bags 81 are stacked and fluidly communicate with each other in the stacking direction. As a specific example, the pressing cuff 71 includes: two layers of air bags 81 fluidly communicating with each other in the stacking direction; the tube 82 provided at one end of one of the air bags 81 in the longitudinal direction; the connection portion 83 provided at the distal end of the tube 82; and the connection plate 84.

The pressing cuff 71 is configured so that the main surface of one of the air bags 81 is fixed to the inner surface of the curler 5. For example, the pressing cuff 71 is attached to the inner surface of the curler 5 by a double-sided tape, an adhesive, or the like.

The two layers of air bags 81 are formed in a rectangular shape elongated in one direction. The air bag 81 is formed by, for example, combining two sheet members 86 elongated in one direction and welding the edges thereof by heat. As a specific example, the two layers of air bags 81 include, from the living body side: a first sheet member 86a; a second sheet member 86b forming the first layer of air bag 81 with the first sheet member 86a; a third sheet member 86c integrally bonded to the second sheet member 86b; and a fourth sheet member 86d forming the second layer of air bag 81 with the third sheet member 86c, as shown in FIGS. 10, 12, and 13.

The first sheet member 86a and the second sheet member 86b form the air bag 81 by the welding of the peripheral edges of the four sides of the sheet members. The second sheet member 86b and the third sheet member 86c are disposed to face each other, and each include a plurality of openings 86b1 and 86c1 that fluidly connect the two air bags 81. The fourth sheet member 86d has an adhesive layer or a double-sided tape on the outer surface thereof on the curler 5 side, and is attached to the curler 5 by the adhesive layer or the double-sided tape.

The third sheet member 86c and the fourth sheet member 86d form the air bag 81 by the welding of the peripheral edges of the four sides of the sheet members. Also, for example, the tube 82 fluidly continuous with the internal space of the air bag 81 is disposed on one side of the third sheet member 86c and the fourth sheet member 86d, and is fixed by welding. For example, the third sheet member 86c and the fourth sheet member 86d form the air bag 81 by the welding of the peripheral edges of the four sides of the sheet members with the tube 82 disposed between the third sheet member 86c and the fourth sheet member 86d, thereby integrally welding the tube 82 thereto.

The tube 82 is connected to one of the two layers of air bags 81, and is provided at one end in the longitudinal direction of the air bag 81. As a specific example, the tube 82 is provided at an end on the curler 5 side of the two layers of air bags 81 and close to the device main body 3. The tube 82 is formed in a tubular shape from a sheet member made of the same material as that of the air bag 81. The tube 82 forms a flow path between the device main body 3 and the air bag 81 in the fluid circuit 7.

The connection portion 83 is formed in a bag shape by welding sheet members 87a and 87b constituting the tube 82 at the distal edge of the tube 82. For example, the connection portion 83 is configured to have a width larger than that of the tube 82, and an outer peripheral edge thereof is formed in an arc shape. The connection portion 83 has an opening 83a formed in a central portion of the sheet member 87b forming the surface facing the device main body 3. The connection portion 83 is configured so that the connection plate 84 is bonded to the sheet member 87b.

The connection plate 84 is a plate-shaped member having rigidity higher than that of the connection portion 83. The connection plate 84 is configured to have a bending elastic modulus of 100 MPa or more at 25° C. in the three-point bending defined by JISK7171, for example. In the present embodiment, the connection plate 84 is formed in a circular plate shape with the outer peripheral edge thereof having the same shape as that of the connection portion 83. Both surfaces of the connection plate 84 are flat. A hole 84a, as a through hole communicating with the opening 83a, is formed in a central portion of the connection plate 84.

The connection plate 84 may be made of a material having a bending elastic modulus higher than that of the sheet members 87a and 87b constituting the connection portion 83, or may be thicker than the connection portion 83. The connection plate 84 may be made of a material which has a bending elastic modulus higher than that of the connection portion 83 and is the same type of resin as that of the connection portion 83, or of a material having a different composition. For example, when a material having the same composition is used, weldability with the connection portion 83 can be improved.

As an example, when the sheet members constituting the connection portion 83 are made of a thermoplastic elastomer of polyurethane of TPUA95 (type A durometer hardness 95) and have a thickness of 0.15 mm, the connection plate 84 is made of a thermoplastic elastomer of polyurethane of TPUD74 (type D durometer hardness 74) and has a thickness of 0.15 mm.

As another example, the connection plate 84 is configured to have a thickness larger than those of the sheet members constituting the connection portion 83. For example, when the sheet members constituting the connection portion 83 are made of a thermoplastic elastomer of polyurethane (TPUA95) and have a thickness of 0.15 mm, the connection plate 84 is made of a thermoplastic elastomer of polyurethane (TPUA95) and has a thickness of 0.6 mm.

A surface on one side of the connection plate 84 is attached to the second adhesive layer 34c of the flow path cover 34. On a surface on the other side of the connection plate 84, the peripheral edge of the hole 84a is welded to the peripheral edge of the opening 83a of the connection portion 83.

The pressing cuff 71 continues to the flow path section 15 formed between the base 33 and the flow path cover 34 from the air bag 81 through the tube 82, the opening 83a formed in the connection portion 83, the hole 84a of the connection plate 84, and the hole 34e of the flow path cover 34.

The back plate 72 is attached to the outer surface 86a1 of the first sheet member 86a of the pressing cuff 71 by an adhesive layer, a double-sided tape, or the like. The back plate 72 is made of a resin material and formed in a plate shape. For example, the back plate 72 is made of polypropylene and formed in a plate shape having a thickness of about 1 mm. The back plate 72 has shape traceability.

The □shape traceability□ refers to a function that allows the back plate 72 to deform so as to trace the shape of a contacted portion of the wrist 100 to be placed; the □contacted portion of the wrist 1000 refers to a region that comes into contact with the back plate 72; and the □contact□ includes both direct and indirect contact.

Therefore, the shape traceability is a function of deforming the back plate 72 provided to the pressing cuff 71 or the back plate 72 provided between the pressing cuff 71 and the sensing cuff 73 to such an extent that the back plate 72 itself or the sensing cuff 73 provided to the back plate 72 conforms to the wrist 100 or comes into close contact with the wrist 100 along the wrist 100.

For example, the back plate 72 includes a plurality of grooves 72a on both main surfaces of the back plate 72 at positions facing each other and at equal distances in the longitudinal direction of the back plate 72. As a result, the portion of the back plate 72 having the grooves 72a is thinner than the portion of the back plate 72 without the grooves 72a, and is thus easily deformed. Accordingly, the back plate 72 has shape traceability of deforming in accordance with the shape of the wrist 100. The back plate 72 is formed to have a length covering the palmar side of the wrist 100. The back plate 72 transmits the pressing force from the pressing cuff 71 to the main surface of the sensing cuff 73 on the back plate 72 side, in a state of conforming to the shape of the wrist 100.

The sensing cuff 73 is fixed to the main surface of the back plate 72 on the living body side. As shown in FIG. 14, the sensing cuff 73 directly contacts the region of the wrist 100 where arteries exist. The sensing cuff 73 is formed in the same shape as that of the back plate 72 or in a shape smaller than that of the back plate 72, in the longitudinal direction and the width direction of the back plate 72. The sensing cuff 73 is inflated to compress a region of the wrist 100 on the palmar side where the arteries 110 exist. The sensing cuff 73 is pressed toward the living body by the inflated pressing cuff 71 via the back plate 72.

As a specific example, the sensing cuff 73 includes one air bag 91, a tube 92 communicating with the air bag 91, and a connection portion 93 provided at a distal end of the tube 92. The sensing cuff 73 is configured so that one of the main surfaces of the air bag 91 is fixed to the back plate 72. For example, the sensing cuff 73 is attached to the main surface of the back plate 72 on the living body side by a double-sided tape, an adhesive layer, or the like.

The air bag 91 is a bag-shaped structure. Since the blood pressure measuring device 1 is configured to use the air with the pump 14 in the present embodiment, an air bag will be described. However, when a fluid other than the air is used, the bag-shaped structure may be a liquid bag or the like. A plurality of air bags 91 described above are stacked and fluidly communicate with each other in the stacking direction.

The air bag 91 is formed in a rectangular shape elongated in one direction. The air bag 91 is formed by, for example, combining two sheet members elongated in one direction and the welding of the edges thereof by heat. As a specific example, the air bag 91 includes a fifth sheet member 96a and a sixth sheet member 96b from the living body side, as shown in FIGS. 10, 12 and 13.

For example, the fifth sheet member 96a and the sixth sheet member 96b are configured so that the tube 92 fluidly continuous with the internal space of the air bag 91 is disposed on one side of the fifth sheet member 96a and the sixth sheet member 96b, and is fixed by welding. For example, the fifth sheet member 96a and the sixth sheet member 96b form the air bag 91 by the welding of the peripheral edges of the four sides of the sheet members with the tube 92 disposed between the fifth sheet member 96a and the sixth sheet member 96b, thereby integrally welding the tube 92 thereto.

The tube 92 is provided at one end in the longitudinal direction of the air bag 91. As a specific example, the tube 92 is provided at an end of the air bag 91 close to the device main body 3. The tube 92 includes a connection portion 93 at its distal end. The tube 92 forms a flow path between the device main body 3 and the air bag 91 in the fluid circuit 7.

The connection portion 93 is formed in a bag shape by welding two sheet members 97a and 97b constituting the tube 92 at the distal edge of the tube 92. For example, the connection portion 93 is configured to have a width larger than that of the tube 92, and an outer peripheral edge thereof is formed in an arc shape. An opening 93a is formed in a central portion of the sheet member 97b forming the surface of the connection portion 93 facing the device main body 3. The connection portion 93 is configured so that a connection plate 94 is bonded to the sheet member 97b.

The connection plate 94 is a plate-shaped member having a bending elastic modulus higher than that of the connection portion 93. The connection plate 94 is configured to have a bending elastic modulus of 100 MPa or more at 25° C. in the three-point bending defined by JISK7171, for example. In the present embodiment, the connection plate 94 is formed in a circular plate shape with the outer peripheral edge thereof having the same shape as that of the connection portion 93. Both surfaces of the connection plate 94 are flat. A hole 94a as a through hole communicating with the opening 93a is formed in a central portion of the connection plate 94.

The connection plate 94 may be made of a material having a bending elastic modulus higher than that of the sheet members 97a and 97b constituting the connection portion 93, or may be thicker than the connection portion 93. The connection plate 94 may be made of a material having the same composition as that of the connection portion 93 or a material having a different composition.

As an example, when the sheet members constituting the connection portion 93 are made of a thermoplastic elastomer of polyurethane (TPUA95) and have a thickness of 0.15 mm, the connection plate 94 is made of a thermoplastic elastomer of polyurethane (TPUD74) and has a thickness of 0.15 mm.

As another example, the connection plate 94 is configured to have a thickness larger than those of the sheet members constituting the connection portion 93.

A surface on one side of the connection plate 94 is attached to the second adhesive layer 34c of the flow path cover 34. On a surface on the other side of the connection plate 94, the peripheral edge of the hole 94a is welded to the peripheral edge of the opening 93a of the connection portion 93.

The sensing cuff 73 continues to the flow path section 15 formed between the base 33 and the flow path cover 34 from the air bag 91 through the tube 92, the opening 93a formed in the connection portion 93, the hole 94a of the connection plate 94, and the hole 34e of the flow path cover 34.

The sheet members 86 and 96 forming the pressing cuff 71 and the sensing cuff 73 are made of a thermoplastic elastomer. For example, thermoplastic polyurethane resin (hereinafter referred to as □TPU□), vinyl chloride resin, ethylene-vinyl acetate resin, thermoplastic polystyrene resin, thermoplastic polyolefin resin, thermoplastic polyester resin, and thermoplastic polyamide resin may be used as the thermoplastic elastomer forming the sheet members 86 and 96. TPU is preferably used as the thermoplastic elastomer. The sheet member may have a single-layer structure or a multi-layer structure.

The sheet members 86 and 96 are not limited to the thermoplastic elastomer, and may be a thermosetting elastomer such as silicone or a combination of a thermoplastic elastomer (for example, TPU) and a thermosetting elastomer (for example, silicone).

When a thermoplastic elastomer is used for the sheet members 86 and 96, a molding method such as T-die extrusion molding or injection molding is adopted, and when a thermosetting elastomer is used for the sheet members 86 and 96, a molding method such as mold casting molding is adopted. The sheet members are molded by the molding method and thereafter sized into a predetermined shape. Then, the sized pieces are bonded by adhesion, welding, or the like to form the air bags 81 and 91 being bag-shaped structures. As a bonding method, a high-frequency welder or laser welding is used when a thermoplastic elastomer is used, and a molecular adhesive is used when a thermosetting elastomer is used.

The fluid circuit 7 is formed of the case 11, the pump 14, the flow path section 15, the on-off valve 16, the pressure sensor 17, the pressing cuff 71, and the sensing cuff 73. Hereinafter, a specific example of the fluid circuit 7 will be described in which the two on-off valves 16 used in the fluid circuit 7 are referred to as a □first on-off valve 16A□ and a □second on-off valve 16B□, and the two pressure sensors 17 used in the fluid circuit 7 are referred to as a □first pressure sensor 17A□ and a □second pressure sensor 17B□.

As shown in FIG. 4, the fluid circuit 7 includes, for example, a first flow path 7a which continues from the pump 14 to the pressing cuff 71, a second flow path 7b which is formed by branching a middle portion of the first flow path 7a and continues from the pump 14 to the sensing cuff 73, and a third flow path 7c which connects the first flow path 7a and the atmosphere. The first flow path 7a includes the first pressure sensor 17A. The first on-off valve 16A is provided between the first flow path 7a and the second flow path 7b. The second flow path 7b includes the second pressure sensor 17B. The second on-off valve 16B is provided between the first flow path 7a and the third flow path 7c.

In the fluid circuit 7 described above, when the first on-off valve 16A and the second on-off valve 16B are closed, only the first flow path 7a is connected to the pump 14, and the pump 14 and the pressing cuff 71 are fluidly connected. In the fluid circuit 7, when the first on-off valve 16A is opened and the second on-off valve 16B is closed, the first flow path 7a and the second flow path 7b are connected, and the pump 14 and the pressing cuff 71, and the pump 14 and the sensing cuff 73 are fluidly connected. In the fluid circuit 7, when the first on-off valve 16A is closed and the second on-off valve 16B is closed, the first flow path 7a and the third flow path 7c are connected, and the pressing cuff 71 and the atmosphere are fluidly connected. In the fluid circuit 7, when the first on-off valve 16A and the second on-off valve 16B are opened, the first flow path 7a, the second flow path 7b, and the third flow path 7c are connected, and the pressing cuff 71, the sensing cuff 73, and the atmosphere are fluidly connected.

Figure 16:
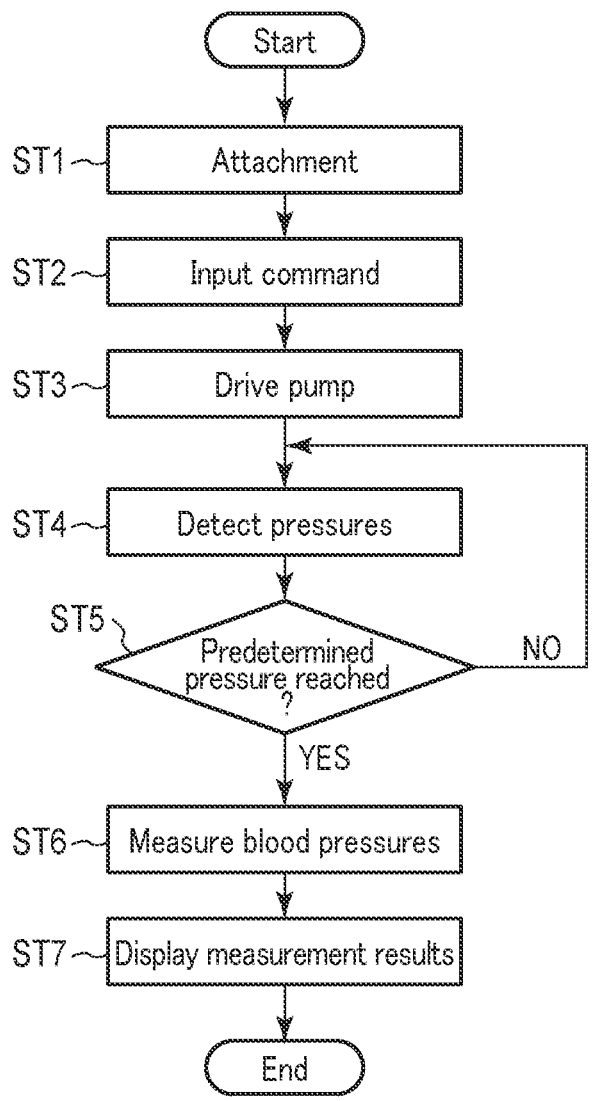
FIG. 16 is a flowchart showing an example of the use of the blood pressure measuring device.
Figure 17:
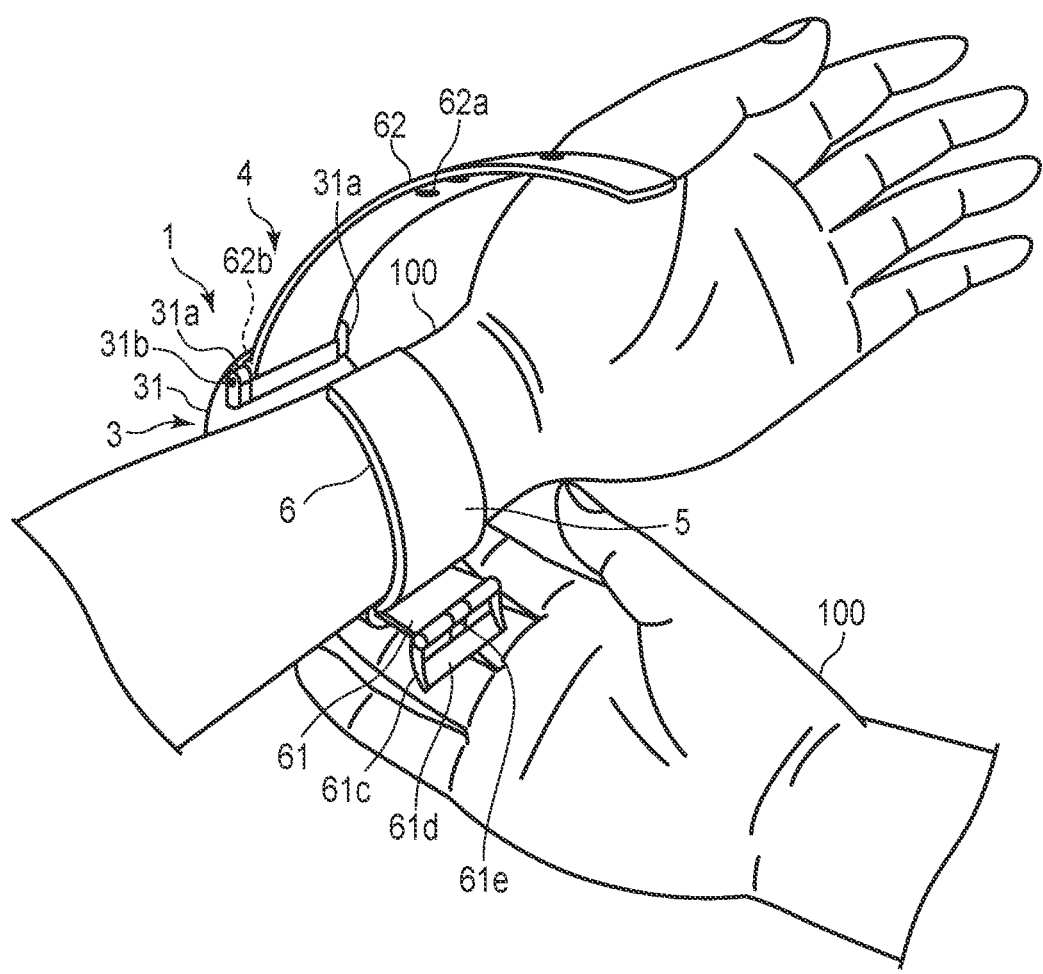
FIG. 17 is a perspective diagram showing an example in which the blood pressure measuring device is worn on a wrist.
Figure 18:
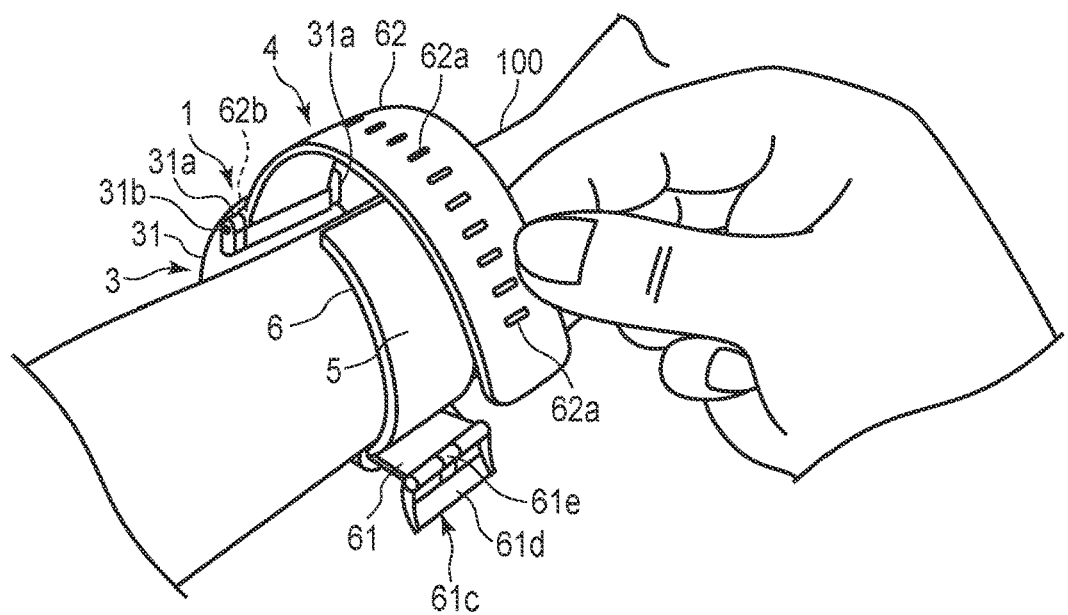
FIG. 18 is a perspective diagram showing an example in which the blood pressure measuring device is worn on a wrist.
Figure 19:
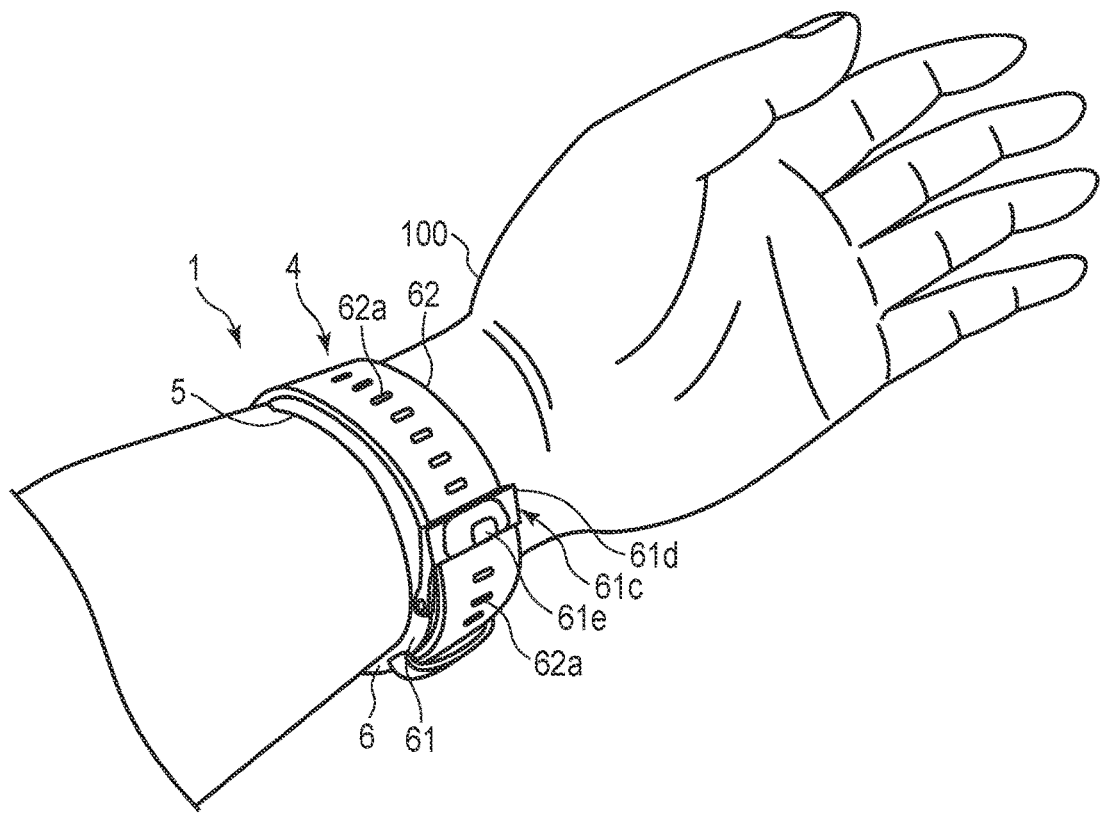
FIG. 19 is a perspective diagram showing an example in which the blood pressure measuring device is worn on a wrist.

Next, an example of measurement of blood pressure values using the blood pressure measuring device 1 will be described with reference to FIGS. 16 to 19. FIG. 16 is a flowchart showing an example of blood pressure measurement using the blood pressure measuring device 1, and shows both the operation of a user and the operation of the controller 55. FIGS. 17 to 19 show an example in which the user wears the blood pressure measuring device 1 on the wrist 100.

First, the user wears the blood pressure measuring device 1 on the wrist 100 (step ST1). As a specific example, the user, for example, inserts one of the wrists 100 into the curler 5, as shown in FIG. 17.

At this time, since the device main body 3 and the sensing cuff 73 are disposed at positions of the curler 5 opposed to each other in the blood pressure measuring device 1, the sensing cuff 73 is disposed in a region of the wrist 100 on the palmar side where the arteries 110 exist. Thus, the device main body 3 is disposed on the dorsal side of the wrist 100. Next, the user passes the second belt 62 through the frame-shaped body 61*d* of the buckle 61*c* of the first belt 61 using the hand opposite to the hand on which the blood pressure measuring device 1 is placed, as shown in FIG. 18. Then, the user pulls the second belt 62, brings the member on the inner peripheral surface side of the curler 5, that is, the cuff structure 6, into close contact with the wrist 100, and inserts the prodding stick 61*e* into the small hole 62*a*. As a result, the first belt 61 and the second belt 62 are connected, and the blood pressure measuring device 1 is worn on the wrist 100, as shown in FIG. 19.

Next, the user operates the operation unit 13 to input a command corresponding to initiation of measurement of blood pressure values. The operation unit 13 in which the input operation of the command has been performed outputs an electric signal corresponding to initiation of measurement to the controller 55 (step ST2). Upon receiving the electric signal, the controller 55, for example, opens the first on-off valve 16A and closes the second on-off valve 16B, drives the pump 14, and supplies compressed air to the pressing cuff 71 and the sensing cuff 73 through the first flow path 7*a* and the second flow path 7*b* (step ST3). Thereby, the pressing cuff 71 and the sensing cuff 73 start to inflate.

The first pressure sensor 17A and the second pressure sensor 17B detect the pressures of the pressing cuff 71 and the sensing cuff 73, and output electric signals corresponding to the detected pressures to the controller 55 (step ST4). Based on the received electric signals, the controller 55 determines whether or not the pressures in the internal spaces of the pressing cuff 71 and the sensing cuff 73 reach a predetermined pressure for measuring blood pressure (step ST5). For example, when the internal pressure of the pressing cuff 71 does not reach the predetermined pressure and the internal pressure of the sensing cuff 73 reaches the predetermined pressure, the controller 55 closes the first on-off valve 16A and supplies compressed air through the first flow path 7*a*.

When both the internal pressure of the pressing cuff 71 and the internal pressure of the sensing cuff 73 reach the predetermined pressure, the controller 55 stops driving the pump 14 (YES in step ST5). At this time, the pressing cuff 71 is sufficiently inflated, and the inflated pressing cuff 71 presses the wrist 100 and the back plate 72, as shown in FIG. 12.

Further, the sensing cuff 73 is sufficiently inflated and pressed toward the wrist 100 by the back plate 72 pressed by the pressing cuff 71. Therefore, the sensing cuff 73 presses the arteries 110 in the wrist 100 to occlude the arteries 110, as shown in FIG. 15.

The controller 55 controls the second on-off valve 16B to repeatedly open and close the second on-off valve 16B or adjust the opening degree of the second on-off valve 16B, thereby increasing the pressure in the internal space of the pressing cuff 71. Based on the electric signal output from the second pressure sensor 17B in the pressurization process, the controller 55 obtains measurement results of blood pressure values, such as systolic blood pressure and diastolic blood pressure, a heart rate, and the like.

The example in which the timing of opening and closing the first on-off valve 16A and the second on-off valve 16B at the time of blood pressure measurement may be suitably set and the controller 55 calculates blood pressure in the process of pressurizing the pressing cuff 71 is described above. However, blood pressure may be calculated in the process of depressurizing the pressing cuff 71 or calculated in both the process of pressurizing the pressing cuff 71 and the process of depressurizing the pressing cuff 71. Next, the controller 55 outputs an image signal corresponding to the obtained measurement results to the display 12.

Upon receiving the image signal, the display 12 displays the measurement results on a screen. The user checks the measurement results by viewing the display 12. After the measurement is completed, the user removes the prodding stick 61*e* from the small hole 62*a*, removes the second belt 62 from the frame-shaped body 61*d*, and removes the wrist 100 from the curler 5, thereby removing the blood pressure measuring device 1 from the wrist 100.

Next, a method of manufacturing the blood pressure measuring device 1 according to an embodiment will be described. The method of manufacturing the blood pressure measuring device 1 includes, as a method of connecting the cuff structure 6 and the device main body 3, a plate bonding step which involves bonding the connection plates 84 and 94 to the connection portions 83 and 93, and an adhering step which involves attaching the connection plates 84 and 94 to the flow path cover 34 on the device main body 3 side.

First, a plate-shaped member molded by a predetermined molding method is sized into a predetermined shape to form the connection plates 84 and 94. In the present embodiment, the plate-shaped members are cut into, for example, a circular shape having holes 84*a* and 94*a* in the center.

In the plate bonding step, the connection plates 84 and 94 are bonded to the connection portions 83 and 93. At this time, the bonding regions Pb of the outer peripheral edges of the openings 83*a* and 93*a* and the holes 84*a* and 94*a* are bonded to each other.

For example, as the bonding method, a high-frequency welder or laser welding is used when a thermoplastic elastomer is used, and a molecular adhesive is used when a thermosetting elastomer is used.

The plate bonding step may be performed at the same time as forming the connection portions 83 and 93 by bonding, through adhesion, welding, or the like, the pieces obtained by sizing the sheet members molded by the molding method into a predetermined shape. For example, when the sheet members 87*a*, 87*b*, 97*a*, and 97*b* are welded to each other, the circular connection plates 84 and 94 are superimposed on the connection portions 83 and 93 at the distal end of the tubes 82 and 92 and are simultaneously bonded to the connection portions 83 and 93. At this time, the openings 83*a* and 93*a* and the holes 84*a* and 94*a* are aligned with each other, and the bonding regions Pb of the outer peripheries of the openings 83*a* and 93*a* and the holes 84*a* and 94*a* are welded to each other.

In the adhering step, after the plate bonding step, for example, one surface of each of the connection plates 84 and 94 that are integrally formed with the sheet members 87*b* and 97*b* in the form of the cuff, is attached to the second adhesive layer 34*c* of the flow path cover 34.

In the blood pressure measuring device 1 according to the embodiment configured as described above, the connection plates 84 and 94 are interposed between the flow path cover 34 of the device main body 3 and the connection portions 83 and 93 of the pressing cuff 71 and the sensing cuff 73; the connection plates 84 and 94 are bonded to the connection portions 83 and 93; and the connection plates 84 and 94 are attached to the flow path cover 34, whereby the cuff structure 6 and the device main body 3 can be easily connected to each other. Therefore, the thickness of the connected part can be reduced as compared to a connection structure using a protrusion or the like.

That is, when a protrusion called a □nipple□ is provided on the cuff side and a protrusion called a □nozzle□ is provided on the supply device side as the connection structure, for example, it is necessary to secure the axial length and thickness of the nozzle and the nipple in order to ensure the function of preventing air leakage and strength, resulting in an increase of the thickness of the connection structure portion.

On the other hand, the blood pressure measuring device 1 according to the embodiment is configured so that the thin plate-shaped connection plates 84 and 94 are directly bonded to the cuff, and that the connection plates 84 and 94 are attached to the flat flow path cover 34, thus making it possible to achieve the connection with a thin bonding structure of about several hundred micrometers. Accordingly, the device configuration can be made thinner and smaller.

Also, when the sheet members 87b and 97b constituting the cuff are directly adhered to the device main body 3 and the cuff is inflated, for example, stresses are applied to the connected part due to deformation of the cuff, causing the adhered part to be easily peeled off. However, since the blood pressure measuring device 1 of the above aspect is configured so that the connection plates 84 and 94 having a high bending elastic modulus are interposed between the device main body 3 and the sheet members 87b and 97b, it is possible to suppress both the deformation of the connected part and the peeling of the adhered part due to the deformation.

In the blood pressure measuring device 1 according to the embodiment, the peripheries of the openings 83a and 93a of the connection portions 83 and 93 and the holes 84a and 94a provided in the connection plates 84 and 94 of the cuff are welded to each other, thereby enabling the flow path section 15 on the device main body 3 side to communicate with the internal spaces of the pressing cuff 71 and the sensing cuff 73.

Since the configuration of adhering the device main body 3 side and the connection plates 84 and 94 using a double-sided adhesive tape or the like allows the connection plates 84 and 94 to be easily peeled off, repair such as replacement of the pressing cuff 71 or the sensing cuff 73 can be easily performed. Also, since the connection plates 84 and 94 are hardly deformed even at the time of repair, the load imposed on the surrounding components at the time of peeling off the connection plates 84 and 94 can be reduced.

Since the blood pressure measuring device 1 according to the embodiment is configured so that the flow path cover 34 includes the metallic base plate 34a, the device has a high rigidity even if it is thin, and hardly deforms. Since the flow path cover 34 includes the adhesive layers 34b and 34c, attachment of the connection plates 84 and 94 can be achieved with ease.

Furthermore, since the blood pressure measuring device 1 according to the embodiment has the adhesive layers 34b and 34c provided around the flow path communicating with the flow path section 15, it is possible to adsorb the dust and suppress the dust from entering the flow path section 15.

The blood pressure measuring device 1 according to the embodiment may also be configured so that the connection plates 84 and 94 are bonded to the cuff structure 6 at the same time as the manufacturing of the cuff structure 6 to be integrally formed with the cuff structure 6, which allows for reduction of the number of manufacturing steps.

Second Embodiment

Next, a blood pressure measuring device 1A according to a second embodiment will be described with reference to FIGS. 20 and 21. The blood pressure measuring device 1A according to the second embodiment has a configuration in which the plurality of connection plates 84 and 94 of the first embodiment described above are integrated and have the same shape as that of the flow path cover 34. Part of the configuration of the present embodiment identical to that of the blood pressure measuring device 1 of the first embodiment will be described using the same reference numerals, and the descriptions and figures thereof will be omitted as appropriate.

Figure 20:
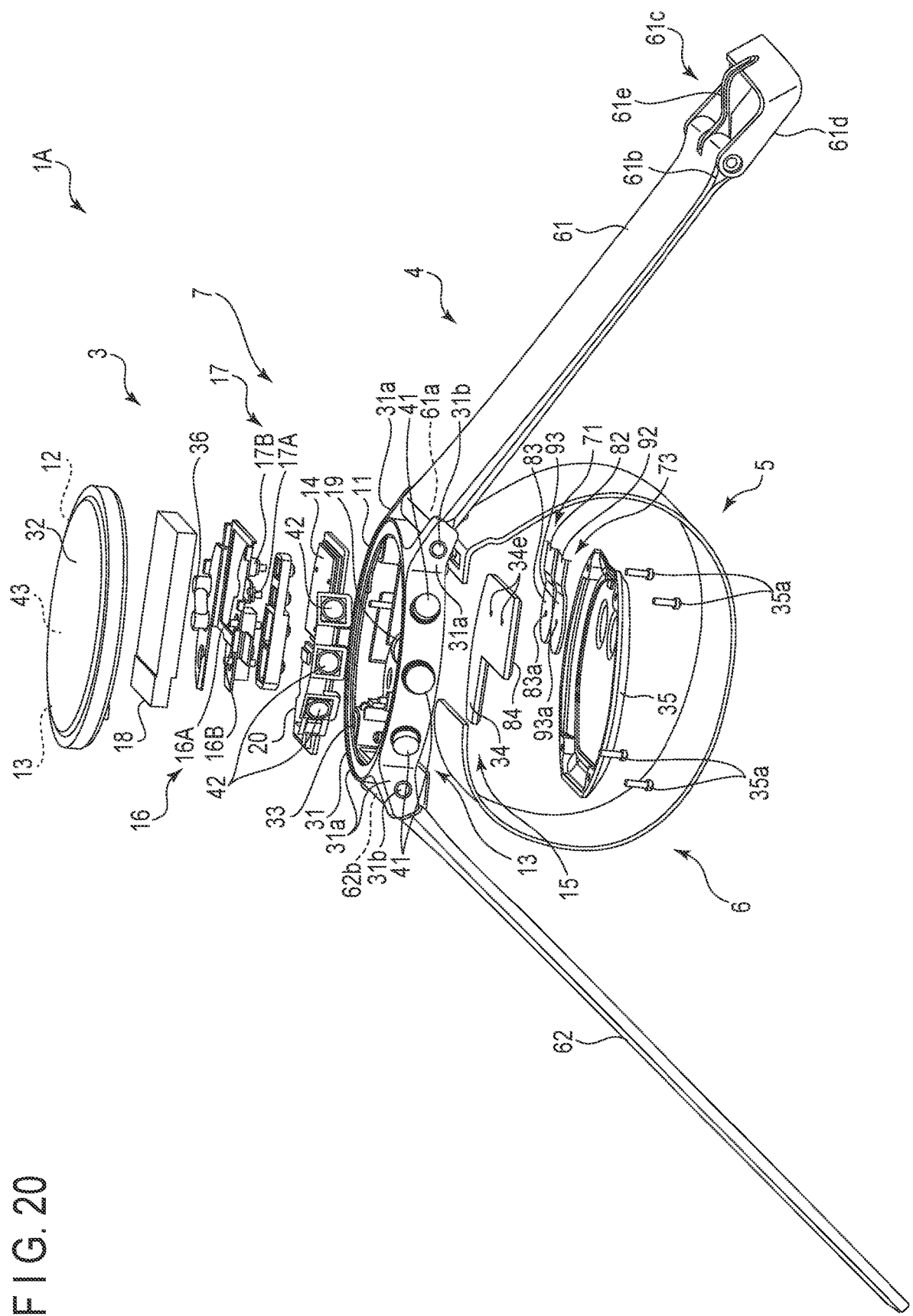
FIG. 20 is an exploded view of a configuration of a blood pressure measuring device according to a second embodiment of the present invention.
Figure 21:
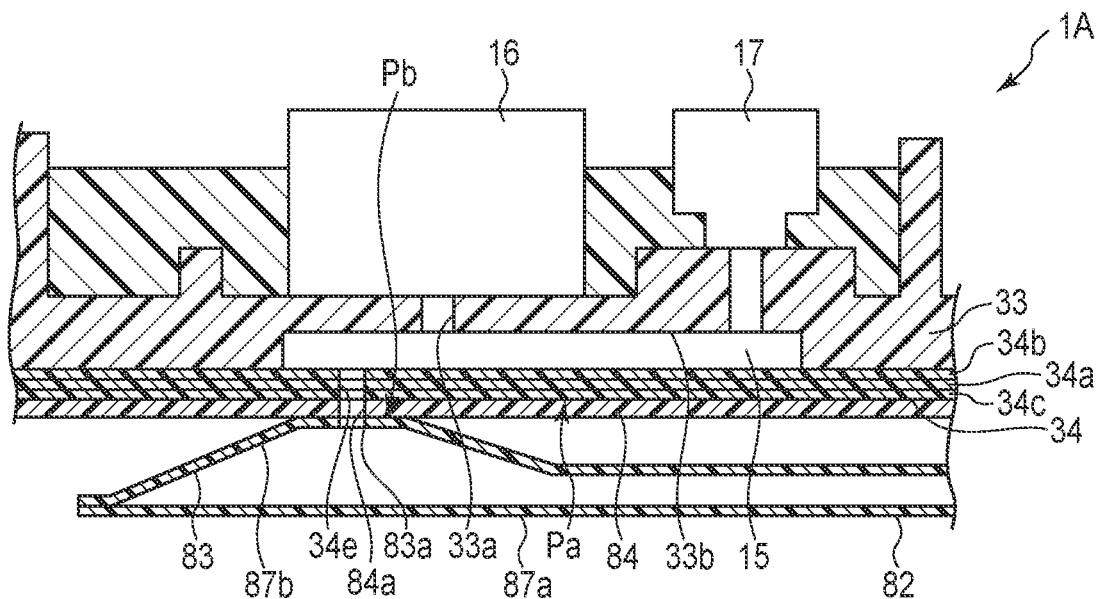
FIG. 21 is a cross-sectional view of a configuration of a connection portion between a device main body and a cuff structure of the blood pressure measuring device.

In the blood pressure measuring device 1A, the connection plate 84 is integrally formed with the flow path cover 34, as shown in FIGS. 20 and 21. In the present embodiment, the connection plate 84 has the same shape as the outer shape of the flow path cover 34, and is attached to the second adhesive layer 34c of the flow path cover 34.

In the connection plate 84, the hole 84a, as a through hole, is formed at a position overlapping the pair of holes 34e of the flow path cover 34. In a manner similar to the connection plates 84 and 94 of the first embodiment, the connection plate 84 has a bending elastic modulus higher than those of the connection portions 83 and 93.

Next, a method of manufacturing the blood pressure measuring device 1A according to an embodiment will be described. The method of manufacturing the blood pressure measuring device 1A includes, as a method of connecting the cuff structure 6 and the device main body 3, a plate bonding step which involves bonding the connection plate 84 to the connection portions 83 and 93, and an adhering step which involves attaching the connection plate 84 to the flow path cover 34 on the device main body 3 side.

First, a plate-shaped member molded by a predetermined molding method is sized into a predetermined shape to form the connection plate 84. For example, in the present embodiment, a plurality of holes 84a are formed at predetermined positions in the connection plate 84, and the connection plate 84 is cut in the same shape as that of the flow path cover 34.

In the plate bonding step, the connection plate 84 is bonded to the connection portions 83 and 93 by high-frequency welder or laser welding. At this time, the bonding regions Pb of the outer peripheral edges of the openings 83a and 93a and the holes 84a and 84a are welded to each other.

In the adhering step, after the plate bonding step, for example, one surface of the connection plate 84 integrally formed with the connection portions 83 and 93 in the form of the cuff is attached to the second adhesive layer 34c of the flow path cover 34.

The blood pressure measuring device 1A and the method of manufacturing the blood pressure measuring device 1A according to the present embodiment achieve the same effects as those of the blood pressure measuring device 1 and the method of manufacturing the blood pressure measuring device 1A according to the first embodiment. That is, since the connection plate 84 having a high bending elastic modulus is interposed at the connected part between the flow path cover 34 and the connection portions 83 and 93, deformation of the connection portions 83 and 93 due to inflation can be prevented, and peeling of the adhered part can be suppressed.

Third Embodiment

Figure 22:
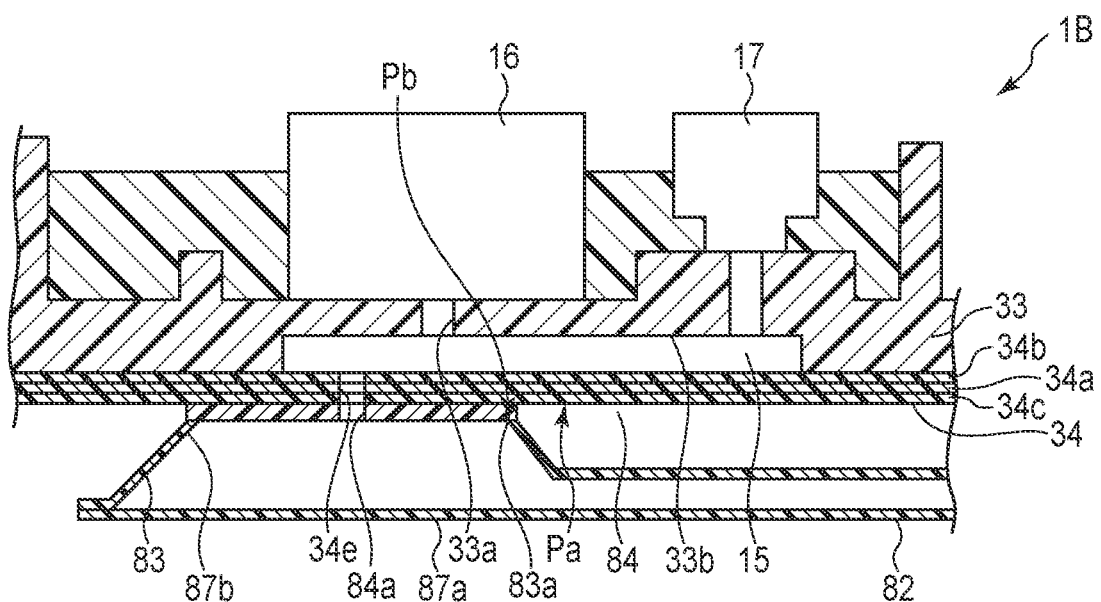
FIG. 22 is a cross-sectional view of a configuration of a connection portion between a device main body and a cuff structure of a blood pressure measuring device according to a third embodiment of the present invention.

Next, a blood pressure measuring device 1B according to a third embodiment will be described with reference to FIG. 22. FIG. 22 is a cross-sectional view of a connection portion of the blood pressure measuring device 1B according to the third embodiment. As shown in FIG. 22, the blood pressure measuring device 1B is configured so that the connection plates 84 and 94 are bonded to the connection portions 83 and 93 at the outer peripheral edges. Part of the configuration of the present embodiment identical to that of the blood pressure measuring device 1 of the first embodiment will be described using the same reference numerals, and the descriptions and figures thereof will be omitted as appropriate.

The present embodiment also achieves the same effects as those of the first embodiment and the second embodiment. That is, since the connection plates 84 and 94 having a high bending elastic modulus are interposed at the connected part between the flow path cover 34 and the connection portions 83 and 93, deformation of the connection portions 83 and 93 due to inflation can be prevented, and peeling of the adhered part can be suppressed.

Fourth Embodiment

Next, a fourth embodiment of the pressing cuff 71 will be described with reference to FIGS. 23 to 25. In the fourth embodiment, the cuff is used in a blood pressure measuring device 1C that is wound around an upper arm to measure blood pressure, instead of the blood pressure measuring device 1 for the wrist 100 according to the first embodiment described above. Part of the configuration of the present embodiment identical to that of the blood pressure measuring device 1 of the first embodiment will be described using the same reference numerals, and the descriptions and figures thereof will be omitted as appropriate.

Figure 23:
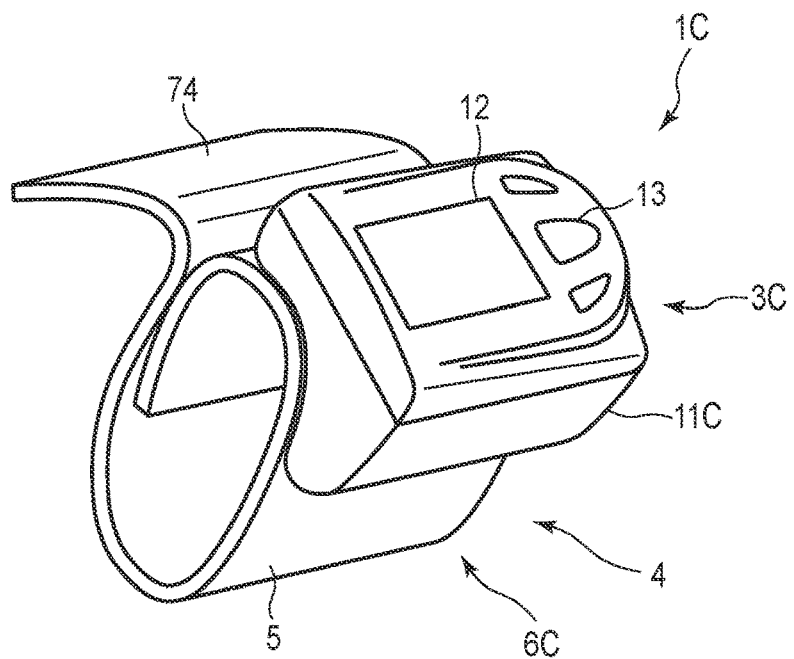
FIG. 23 is a perspective view of a configuration of a blood pressure measuring device according to a fourth embodiment of the present invention.
Figure 24:
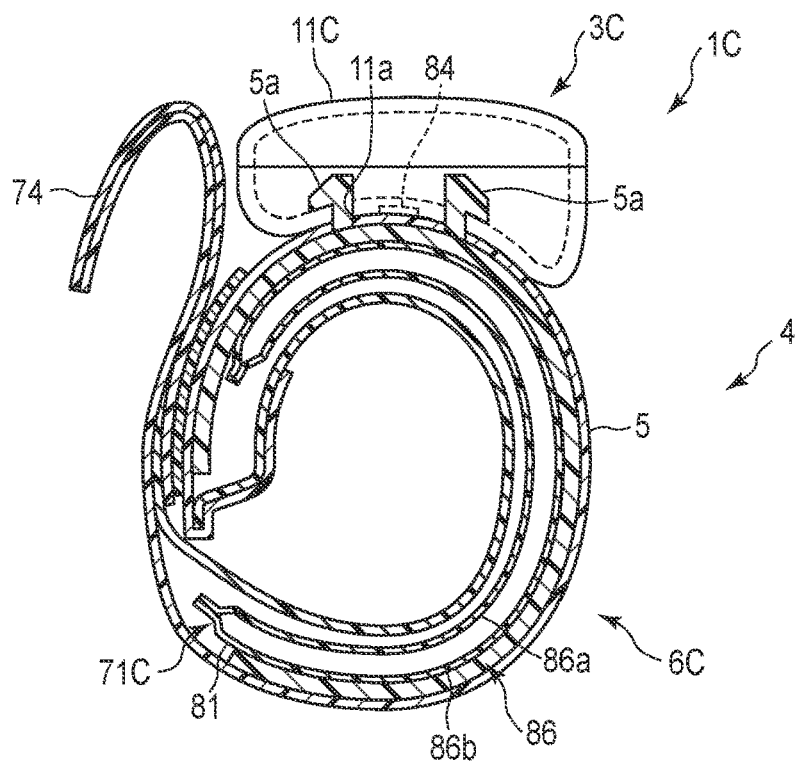
FIG. 24 is a cross-sectional view of a configuration of the blood pressure measuring device.

For example, the blood pressure measuring device 1C of the second embodiment includes a device main body 3C and a cuff structure 6C, as shown in FIGS. 23 to 25. The device main body 3C includes, for example, a case 11C, a display 12, an operation unit 13, a pump 14, a flow path section 15, an on-off valve 16, a pressure sensor 17, a power supply unit 18, and a control substrate 20. As shown in FIG. 25, the device main body 3C includes one pump 14, one on-off valve 16, and one pressure sensor 17.

For example, the case 11C is formed in a box shape. The case 11C includes an attachment portion 11a for fixing the cuff structure 6C. The attachment portion 11a is, for example, an opening provided on the back surface of the case 11C.

As shown in FIGS. 23 to 25, the cuff structure 6C includes a curler 5, a pressing cuff 71C provided on the living body side of the curler 5, and a bag-shaped cover body 74 made of cloth or the like in which the curler 5 and the pressing cuff 71C are disposed. The cuff structure 6C is wound around an upper arm.

The curler 5 includes, for example, a protrusion 5a fixed to the attachment portion 11a.

The pressing cuff 71C is accommodated in the bag-shaped cover body 74 together with the curler 5, and is fixed to the inner surface of the curler 5. For example, the pressing cuff 71C is attached to the inner surface of the curler 5 by a double-sided tape or an adhesive.

The air bag 81 is formed in a rectangular shape elongated in one direction. The air bag 81 is formed by, for example, combining two sheet members 86 elongated in one direction and welding the edges thereof by heat. As a specific example, the air bag 81 includes, from the living body side, a first sheet member 86a, and a second sheet member 86b forming the air bag 81 with the first sheet member 86a, as shown in FIG. 23.

The cuff structure 6C is connected to the device main body 3C via the connection plate 84 having a bending elastic modulus higher than those of the sheet members of the cuff structure 6C. Specifically, the outer peripheral portion of the opening formed in the connection portion of the cuff structure 6C and the outer peripheral portion of the hole 84a in the surface on the other side (the lower side in the drawing) of the connection plate 84 are bonded to each other by welding or the like. On the other hand, the surface on one side (the upper side in the drawing) of the connection plate 84 is attached to the device main body 3C by an adhesive layer of an adhesive material, an adhesive tape, or the like. The cuff structure 6C and the device main body 3C are configured so that the flow path section 15 and the internal space of the cuff structure 6C communicate with each other through the hole 84a and the opening.

In the blood pressure measuring device 1C configured as described above, the connection plate 84 with a high bending elastic modulus bonded to the cuff is attached to the device main body 3C side, in a manner similar to the above-described blood pressure measuring device 1, whereby the device main body 3C and the cuff structure 6C can be easily connected to each other, and peeling of the attached part and air leakage can be suppressed by preventing deformation of the connected part. Also, reduction of the thickness can be achieved as compared to a connection structure using a protrusion such as a nipple.

The shape and size of the connection plate 84 are not limited to those described in the above embodiment. For example, a pair of cuffs may be bonded to one connection plate 84.

The configuration of the base plate 34a of the flow path cover 34 is not limited to that described in the above embodiment. For example, a resin plate may be used instead of a metal plate.

The flow path cover 34 may be integrally formed as the connection plate 84. The flow path cover 34 is formed in a plate shape having a bending elastic modulus higher than that of the connection portion 83. The flow path cover 34 includes, for example, the base plate 34a and the first adhesive layer 34b disposed on one side of the base plate 34a. In the present embodiment, the base plate 34a is formed of, for example, a resin layer having a hardness higher than that of the connection portion 83. In the present embodiment, for the plate bonding step, the connection portion 83 is positioned in a region including the hole 34e and on the other surface of the flow path cover 34 as the connection plate 84, and the connection portions 83 and 93 are welded in a bonding region around the hole 34e. Then, for the adhering step, the first adhesive layer 34b of the flow path cover 34 to which the connection portion 83 is bonded is attached to the base 33.

The present embodiment also achieves the same effects as those of the first embodiment and the second embodiment.

That is, since the connection portion 83 and the flow path cover 34 are configured to have a high bending elastic modulus, deformation of the connection portion 83 due to inflation can be prevented, and peeling of the adhered part can be suppressed. Also, since the connection plate 84 is integrally formed as the flow path cover 34, the number of components and the number of connection steps can be reduced.

In addition, an adhesive may be disposed as the adhesive layers 34b and 34c instead of a double-sided tape, and the bonding of the connection plates 84 and 94 and the connection portions 83 and 93 is not limited to welding and may take the form of adhesion.

The above-described embodiments are merely examples of the present invention in all respects. It goes without saying that various improvements and modifications can be made without departing from the scope of the present invention. In other words, in the implementation of the present invention, a specific configuration according to the embodiment may be adopted as appropriate.

REFERENCE SIGNS LIST

1. Blood pressure measuring device
1C. Blood pressure measuring device
3. Device main body
3C. Device main body
4. Belt
5. Curler
5a. Protrusion
6. Cuff structure
6C. Cuff structure
7. Fluid circuit
7a. First flow path
7b. Second flow path
7c. Third flow path
11. Case
11a. Attachment portion
11C. Case
12. Display
13. Operation unit
14. Pump
15. Flow path section
16. On-off valve
16A. First on-off valve
16B. Second on-off valve
17. Pressure sensor
17A. First pressure sensor
17B. Second pressure sensor
18. Power supply unit
19. Vibration motor
20. Control substrate
30. Base
31. Outer case
31a. Lug
31b. Spring bar
32. Windshield
35. Back cover
35a. Screw
36. Flow path tube
41. Button
42. Sensor
43. Touch panel
51. Substrate
52. Acceleration sensor
53. Communication unit
54. Storage
55. Controller
61. First belt
61a. First hole
61b. Second hole
61c. Buckle
61d. Frame-shaped body
61e. Prodding stick
62. Second belt
62a. Small hole
71. Pressing cuff
71A. Pressing cuff
71B. Pressing cuff
71C. Pressing cuff
72. Back plate
72a. Groove
73. Sensing cuff
74. Bag-shaped cover body
81. Air bag
82. Tube
83. Connection portion
83a. Opening
84. Connection plate
84a. Hole
86. Sheet member
86a. First sheet member
86a1. Outer surface
86b. Second sheet member
86b1. Opening
86c. Third sheet member
86c1. Opening
86d. Fourth sheet member
87a, 87b. Sheet member
91. Air bag
92. Tube
93. Connection portion
93a. Opening
94. Connection plate
94a. Hole
96. Sheet member
96a. Fifth sheet member
96b. Sixth sheet member
97a, 97b. Sheet member
100. Wrist
110. Artery

The invention claimed is:

1. A blood pressure measuring device comprising:
a device main body configured to form a flow path of a fluid and supply the fluid, the device main body comprising:
a base with a flow path section;
a pump disposed on one side of the base;
a flow path cover disposed to face another side of the base to cover the flow path section; and
a back cover disposed on another side of the flow path cover; and
a cuff configured to be wound around a living body, the cuff comprising:
a plurality of tubes formed by welding sheet members together;
a plurality of connection portions, each connection portion having an opening and being disposed at a distal edge of a respective tube of the plurality of tubes, and each connection portion being formed as a bag by the welding of the sheet members together; and
a plurality of connection plates, each connection plate having a hole communicating with a respective opening of the connection portions, and having a bending elastic modulus higher than that of the connection portion, the connection plate being bonded to the connection portion and adhered to the device main body, wherein the cuff is configured to be inflated when the fluid is supplied to an internal space of the cuff, the connection plate is formed in a plate shape and has a first surface and a second surface, both the first surface of the connection plate and the second surface of the connection plate being flat, the connection plate is disposed between the flow path cover and the back cover, the first surface of the connection plate is adhered to the flow path cover by an adhesive layer, the second surface of the connection plate is bonded to the connection portion of the cuff, and on the second surface, which opposes the first surface, peripheral edges of the hole in each connection plate are welded to the peripheral edges of the opening in each connection portion.

2. The blood pressure measuring device according to claim 1, wherein the cuff comprises:

a pressing cuff and a sensing cuff, each including an internal space, the plurality of connection portions being configured to communicate with the internal space of the pressing cuff and the internal space of the sensing cuff, and the internal space of the pressing cuff and the internal space of the sensing cuff are configured to communicate with the flow path via the opening in each connection portion and the hole in each connection plate.

3. The blood pressure measuring device according to claim 1, wherein the flow path cover comprises:

a base plate;

a first adhesive layer disposed on one side of the base plate; and a second adhesive layer disposed on another side of the base plate, and the connection plate is attached to the second adhesive layer.

* * * * *